United States Patent [19]

Kucherlapati et al.

[11] Patent Number: 6,150,584

[45] Date of Patent: Nov. 21, 2000

[54] HUMAN ANTIBODIES DERIVED FROM IMMUNIZED XENOMICE

[75] Inventors: Raju Kucherlapati, Darien, Conn.; Aya Jakobovits, Menlo Park, Calif.; Daniel G. Brenner, Redwood City, Calif.; Daniel J. Capon, Hillsborough, Calif.; Sue Klapholz, Stanford, Calif.

[73] Assignee: Abgenix, Inc., Fremont, Calif.

[21] Appl. No.: 08/724,752

[22] Filed: Oct. 2, 1996

Related U.S. Application Data

[63] Continuation-in-part of application No. 08/430,938, Apr. 27, 1995, abandoned, which is a continuation-in-part of application No. 08/234,143, Apr. 28, 1994, abandoned, and a continuation-in-part of application No. 08/112,848, Aug. 27, 1993, abandoned, and a continuation-in-part of application No. 08/031,801, Mar. 15, 1993, and a continuation-in-part of application No. 07/919,297, Jul. 24, 1992, abandoned, and a continuation-in-part of application No. 07/610,515, Nov. 8, 1990, abandoned, and a continuation-in-part of application No. 07/466,008, Jan. 12, 1990, abandoned, and a continuation-in-part of application No. PCT/US96/05928, Apr. 29, 1996.

[51] Int. Cl.$^7$ ............................. A61K 48/00; C12N 5/10; C12N 15/07

[52] U.S. Cl. ................................. 800/18; 800/6; 800/25; 424/93.21

[58] Field of Search .............................. 800/2, 6, 25, 18; 424/93.21

[56] References Cited

U.S. PATENT DOCUMENTS

| | | | |
|---|---|---|---|
| 4,950,599 | 8/1990 | Bertling | 435/456 |
| 4,959,313 | 9/1990 | Taketo | 435/69.1 |
| 5,204,244 | 4/1993 | Fell et al. | 435/68 |
| 5,545,806 | 8/1996 | Lonberg et al. | 800/6 |
| 5,545,807 | 8/1996 | Surani et al. | 800/6 |
| 5,569,825 | 10/1996 | Lonberg et al. | 800/18 |

FOREIGN PATENT DOCUMENTS

| | | | |
|---|---|---|---|
| 0 298 807 A1 | 6/1988 | European Pat. Off. | |
| 0 315 062 B1 | 5/1989 | European Pat. Off. | |
| 0 322 240 B1 | 6/1989 | European Pat. Off. | |
| 0 459 372 A3 | 5/1991 | European Pat. Off. | |
| 0 463 151 B1 | 1/1992 | European Pat. Off. | |
| WO 90/04036 | 4/1990 | WIPO. | |
| WO 91/00906 | 1/1991 | WIPO. | |
| WO 91/10741 | 7/1991 | WIPO. | |
| WO 92/03918 | 3/1992 | WIPO. | |
| WO 93/05165 | 3/1993 | WIPO | C12N 15/87 |
| WO94/00569 | 1/1994 | WIPO | C12N 15/00 |
| WO 94/02602 | 2/1994 | WIPO. | |

OTHER PUBLICATIONS

Patent Abstracts of Japan, vol. 13, No. 186 (E–752) (3534), May 2, 1989 Japanese Application 63–11 1378 (Hitachi).

Patent Abstracts of Japan, vol. 13, No. 254 (E–772) (3602), Jun. 13, 1989 Japanese Appln. 63–151680 (Sumitomo Electric).

Japanese Patent Abstract of Japan, vol. 6, No. 95(E–110) (973), Jun. 3, 1982, Japanese Appln. 57–27079 (Nippon Denshin).

Wu et al., "High Temperature Processing of Cuprate Oxide Superconductors" *Applied Physics Letters*, vol. 52, No. 22, May 30, 1988.

Patent Abstracts of Japan, vol. 13, No. 144 (E–740) (3492), Apr. 10, 1989 Japanese Appliction 63–306676 (Matsushita Electric).

Albertson, et al., "Construction and characterization of a yeast artificial chromosome library containing seven haploid human genome equivalents," *Proc. Natl. Acad. Sci. U.S.A.* 87:4256–4260 (1990).

Ayares, et al., "Sequence homology requirements for intermolecular recombination in mammalian cells," *Proc. Natl. Acad. Sci. U.S.A.* 83:5199–5203 (1986).

Berman, et al., "Content and organization of the human Ig $V_h$ locus: definition of three new $V_h$ families and linkage to the Ig $C_h$ locus" *EMBO J* 7:727–738 (1988).

Blankenstein, et al., "Immunoglobulin $V_h$ region genes of the mouse are organized in overlapping clusters" *Eur. J. Immunol.* 17:1351–1357 (1987).

Brinster, et al., "Introns increase transcriptional efficiency in transgenic mice," *Proc. Natl. Acad. Sci. U.S.A.* 85:836–840 (1988).

Brownstein, et al., "Isolation of single–copy human genes from a library of yeast artificial chromosomes", *Science* 244:1348–1351 (1989).

Bruggemann, et al., "Construction, function and immunogenicity of recombinant monoclonal antibodies," *Behring Inst. Mitt.* 87:21–24 (1990).

Bruggemann, et al., "Human antibody production in transgenic mice: expression from 100 kb of the human IgH locus," *Eur. J. Immunolog.* 21:1323–1326 (1991).

Bruggemann, et al., "A repertoire of monoclonal antibodies with human heavy chains from transgenic mice," *Proc. Natl. Acad. Sci. U.S.A.* 86:6709–6713 (1989).

Burke, et al., "Cloning of large segments of exogenous DNA into yeast by means of artificial chromosome vectors," *Science* 236:806–812 (1987).

Buttin, et al., "Exogenous Ig rearrangement in transgenic mice: a new strategy for human monoclonal antibody production," *Trends in Genetics* 3(8):205–206 (1987).

Davies, et al., 1992, "Targeted alterations in yeast artificial chromosomes for inter–species gene transfer," *Nucleic Acids Res.* 20:2693–2698 (1992).

(List continued on next page.)

*Primary Examiner*—Karen M. Hauda
*Attorney, Agent, or Firm*—Fish & Neave; James F. Haley, Jr.; Jane T. Gunnison

[57] ABSTRACT

Fully human antibodies against a specific antigen can be prepared by administering the antigen to a transgenic animal which has been modified to produce such antibodies in response to antigenic challenge, but whose endogenous loci have been disabled. Various subsequent manipulations can be performed to obtain either antibodies per se or analogs thereof.

12 Claims, 18 Drawing Sheets

OTHER PUBLICATIONS

Dorfman, N.A. "The optimal technological approach to the development of human hybridomas," *Journal of Biological Response Modifiers* 4:213–239 (1986).

Eliceiri, et al., "Stable integration and expression in mouse cells of yeast artificial chromosomes harboring human genes," *Proc. Natl. Acad. Sci. U.S.A.* 88:2179–2183 (1991).

Garza, et al., "Mapping the drosophila genome with yeast artificial chromosomes with yeast artificial chromosomes", *Science* 246:641–646 (1989).

Gnirke, et al., "Cloning and in vivo expression of the human GART gene using yeast artificial chromosomes", *EMBO Journal* 10(7):1629–16–14 (1991).

Huxley, et al., "The human HPRT gene on a yeast artificial chromosome is functional when transferred to mouse cells by cell fusion," *Genomics* 9:742–750 (1991).

Joyner, et al., "Production of a mutation in mouse En–2 gene by homologous recombination in embryonic stem cells," *Nature* 338:153–155 (1989).

Koller, et al., "Inactivating the β2–microglobulin locus in mouse embryonic stem cells by homologous recombination" *Proc. Nat'l Acad. Sci.* 86:8932–8935 (1989).

Kucherlapati, R., "Homologous recombination in mammalian somatic cells," *Prog. Nucleic Acid Res. Mol. Biol.* 36:301–310 (1989).

Matsuda, et al., "Structure and physical map of 64 variable segments in the 3'0.8–megabase region of the human immunoglobulin heavy chain locus," *Nature Genetics* 3:88–94 (1993).

Mortensen, et al., "Production of homozygous mutant ES cells with a single targeting construct," *Mol. Cell. Biol.* 12(5):2391–2395 (1991).

Pachnis, et al., "Transfer of a yeast artificial chromosome carrying human DNA from *Saccharomyces cerevisiae* into mammalian cells," *Proc. Natl. Acad. Sci. U.S.A.* 87:5109–5113 (1990).

Pavan, et al., "Modification and transfer into an embryonal carcinoma cell line of a 360–kilobase human–derived yeast artificial chromosome," *Mol. Cell. Biol.* 10(8):4163–4169 (1990).

Sakano, et al., "Identification and nucleotide sequence of a diversity DNA segment (D) of immunoglobulin heavy chain genes," *Nature* 290:562–565 (1981).

Shimizu, et al., "Immunoglobulin double–isotype expression by trans–mRNA in a human immunoglobulin transgenic mouse," *Proc. Natl. Acad. Sci. U.S.A.* 86:8020–8023 (1989).

Shin, et al., "Physical map of the 3' region of the human immunoglobulin heavy chain locus: clustering of autoantibody–related variable segments in one haplotype," *EMBO* 10:3641–3645 (1991).

Taggart, et al., "Stable antibody–producing murine hybridomas," *Science* 219:1228–1230 (1983).

Thomas, et al., "Site–directed mutagenesis by gene targeting in mouse embryo–derived stem cells," *Cell* 51:503–512 (1987).

Traver, et al., "Rapid screening of a human genomic library in yeast artificial chromosomes for single–copy sequences," *Proc. Natl. Acad. Sci. U.S.A.* 86:5898–5902 (1989).

Tucker, et al., "Mouse IgA heavy chain gene sequence: implications for evolution of immunoglobulin hinge exons," *Proc. Natl. Acad. Sci. U.S.A.* 78:7684–7688 (1981).

Yamamura, et al., "Cell–type specific and regulated expression of a human yl heavy–chain immunoglobulin gene in transgenic mice", *Proc. Natl. Acad. Sci. U.S.A.* 83:2152–2156 (1986).

Yancoupoulos and Alt, *Cell* 40:271–281 (1985).

Zachau, The human immunoglobulin κ locus and some of its acrobatics, *Biol. Chem.* 371: 1–6 (1990).

Aldhous, "Transgenic mice display a class (switching) act," *Science* 262:1212–1213 (1993).

Berman, et al., "Content and organization of the human Ig $V_H$ locus: definition of three new $V_H$ families and linkage to the Ig $C_H$ locus," *EMBO Journal* 7(3):727–738 (1988).

Brüggemann, et al., "A repertoire of monoclonal antibodies with human heavy chains from transgenic mice," *Proc. Natl. Acad. Sci USA* 86:6709–6713 (1989).

Choi, et al., "RNA splicing generates a variant light chain from an aberrantly rearranged K gene," *Nature* 286:776–779 (1980).

Choi, et al., "Transgenic mice containing a human heavy chain immunoglobulin gene fragment cloned in a yeast artificial chromosome," *Nature Genetics* 4:117–123 (1993).

Jakobovits, et al., "Germ–line transmission and expression of a human–derived yeast artificial chromosome," *Nature* 362:255–258 (1993).

Joyner, et al., "Production of a mutation in mouse En–2 gene by homologous recombination in embryonic stem cells," *Nature* 338:153–156 (1989).

Max, et al., "Sequences of five potential recombination sites encoded close to an immunoglobulin k constant region gene," *Proc. Natl. Acad. Sci. USA* 76(7):3450–3454 (1979).

Miller, et al., "Structural alterations in J regions of mouse immunoglobulin λ genes are associated with differential gene expression," *Nature* 295:428–430 (1982).

Morrison, S. "Success is in the Specification," *Nature*, 369, pp. 812–813 (1994).

Orkin, et al., "Mutation in an intervening sequence splice junction in man," *Proc. Natl. Acad. Sci. USA* 78(8):5041–5045 (1981).

Rajewsky, et al., "Evolutionary and somatic selection of the antibody repertoire in the mouse," *Science* 238:1088–1094 (1987).

Ramirez–Solis, et al., "Chromosome engineering in mice," *Nature* 378:720–724 (1995).

Sakano, et al., "Sequences at the somatic recombination sites of immunoglobulin light–chain genes," *Nature* 280:288–294 (1979).

Sakano, et al., "Two types of somatic recombination are necessary for the generation of complete immunoglobulin heavy–chain genes," *Nature* 286:676–683 (1980).

Schedl, et al., "A method for the generation of YAC transgenic mice by pronuclear microinjection," *Nucleic Acids Research* 21(20):4783–4787 (1993).

Schedl, et al., "A yeast artificial chromosome covering the tyrosinase gene confers copy number–dependent expression in transgenic mice," *Nature* 362:258–261 (1993).

Seidman, et al., "A Mutant immunoglobulin light chain is formed by aberrant DNA– and RNA–splicing events," *Nature* 286:779–783 (1980).

Shimizu, et al., "Immunoglobulin double–isotype expression by trans–mRNA in a human immunoglobulin transgenic mouse," *Proc. Natl. Acad. Sci, USA* 86:8020–8023 (1989).

Strauss, et al., "Germ line transmission of a yeast artificial chromosome spanning the murine $α_1$ (1) collagen locus," *Science* 259:1904–1907 (1993).

Capecchi et al., "Altering The Genome By Homologous Recombination," (1989) 244:1288–92.

Doetschman et al., "Targeted Mutation Of The HPRT Gene In Mouse Embryonic Stem Cells," (1988) 85:8583–8587.

Johnson et al., "Targeting Of Nonexpressed Genes in Embryonic Stem Cells Via Homologous Recombination," (1989) 245:1234–1236.

Mansour et al., "Disruption of the Proto–oncogene int–2 in Mouse Embryo–derived Stem Cells: A General Strategy For Targeting Mutations To Non–selectable Genes," (1988) 336:348–352.

Schedl et al., "Transgenic Mice Generated By Pronuclear Injection Of A Yeast Artificial Chromosome," (1992) 20:3073–3077.

Schwartzberg et al., "Germ–line Transmission Of A c–abl Mutation Produced By Targeted Gene Disruption in ES Cells," (1989) 246:799–803.

Treisman et al., "Specific Transcription and RNA Splicing Defects in Five Cloned $\beta$–Thalassaemia Genes," (1983) 302:591–596.

Zjilstra et al., "Germ–line Transmission Of A Disrupted $\beta$2–Microglobulin Gene Produced By Homologous Recombination in Embryonic Stem Cells," (1989) 342:435–438.

Green, L.L. et al., "Antigen–specific human monoclonal antibodies from mice engineered with human Ig heavy and light chain YACs," *Nat Genet.* 7, pp. 13–21 (1994).

Emery, S.C. and Adair, J.R., "Humanised monoclonal Antibodies for Therapeutic Applications," *Expert Opinion on Investigation Drugs*, 3, pp. 241–251 (1994).

```
                         CDR1
Germline    VH6       AGACCCTCTC ACTCACCTGT GCCATCTCCG GGGACAGTGT CTCTAGCAAC  50
Hybridoma   D5.1.4    AGACCCTCTC ACTCACCTGT GCCATCTCCG GGGACAGTGT CTCTAGCGAC  50
Germline    JH4       ────────── ────────── ────────── ────────── ──────────
Germline    D(N1)     ────────── ────────── ────────── ────────── ──────────
Germline    hMu       ◄───────── ────────── ────────── ────────── ──── VH6 ─

CDR2
Germline    VH6       AGTGCTGCTT GGAACTGGAT CAGGCAGTCC CCATCGAGAG GCCTTGAGTG 100
Hybridoma   D5.1.4    AGTGCTGCTT GGAACTGGAT CAGGCAGTCC CCATCGAGAG GCCTTGAGTG 100
Germline    JH4       ────────── ────────── ────────── ────────── ──────────
Germline    D(N1)     ────────── ────────── ────────── ────────── ──────────
Germline    hMu       ────────── ────────── ────────── ────────── ──────────
                      ────────────────── VH6 ──────────────────────►

Germline    VH6       GCTGGGAAGG ACATACTACA GGTCCAAGTG GTATAATGAT TATGCAGTAT 150
Hybridoma   D5.1.4    GCTGGGAAGG ACATACTACA GGTCCAAGTG GTATAATGAT TATGCAGTTT 150
Germline    JH4       ────────── ────────── ────────── ────────── ──────────
Germline    D(N1)     ────────── ────────── ────────── ────────── ──────────
Germline    hMu       ────────── ────────── ────────── ────────── ──────────
                      ────────────────── VH6 ──────────────────────►

Germline    VH6       CTGTGAAAAG TCGAATAACC ATCAACCCAG ACACATCCAA GAACCAGTTC 200
Hybridoma   D5.1.4    CTGTGAAAAG TCGAATAACC ATCAACCCAG ACACATCCAA GAACCAGTTC 200
Germline    JH4       ────────── ────────── ────────── ────────── ──────────
Germline    D(N1)     ────────── ────────── ────────── ────────── ──────────
Germline    hMu       ────────── ────────── ────────── ────────── ──────────
                      ────────────────── VH6 ──────────────────────►

Germline    VH6       TCCCTGCAGC TGAACTCTGT GACTCCCGAG GACACGGCTG TGTATTACTG 250
Hybridoma   D5.1.4    TCCCTGCAGC TGAACTCTGT GACTCCCGAG GACACGGCTG TGTATTACTG 250
Germline    JH4       ────────── ────────── ────────── ────────── ──────────
Germline    D(N1)     ────────── ────────── ────────── ────────── ──────────
Germline    hMu       ────────── ────────── ────────── ────────── ──────────
                      ────────────────── VH6 ──────────────────────►

Germline    VH6       TGCAAGAGA─ ────────── ────────── ────────── ──────────  259
Hybridoma   D5.1.4    TGCAAGAGAT ATAGCAGTGG CTGGCGTCCT CTTTGACTGC TGGGGCCAGG  300
Germline    JH4       ────────── ────────── ────────── ─ CTTGACTAGC TGGGGCCAAG  20
Germline    D(N1)     ──────── ─T ATAGCAGCAG CTGG────── ────────── ──────────  15
Germline    hMu       ────────── ────────── ────────── ────────── ──────────
                      ── VH6 ──►│◄── DN1 ──│    │◄──── JH4 ────────
```

FIG.12A

```
Germline   VH6     ─────────── ─────────── ─────────── ─────────── ─────────── 259
Hybridoma  D5.1.4  GAACCCTGGT  CACCGTCTCC  TCAGGGAGTG  CATCCGCCCC  AACCCTTTTC  350
Germline   JH4     GAACCCTGGT  CACCGTCTCC  TCA──────── ─────────── ─────────── 43
Germline   D(N1)   ─────────── ─────────── ─────────── ─────────── ─────────── 15
Germline   hMu     ─────────── ─────────── ───GGGAGTG  CATCCGCCCC  AACCCTTTTC  27
                   ─────── JH4 ───────▶|◀─── hμ ───

Germline   VH6     ─────────── ─────────── ─────────── ─────────── ─────────── 259
Hybridoma  D5.1.4  CCCCTCGTCT  CCTGTGAGAA  TTCCCCGTCG  GATACGAGCA  GCGTGGCCGT  400
Germline   JH4     ─────────── ─────────── ─────────── ─────────── ─────────── 43
Germline   D(N1)   ─────────── ─────────── ─────────── ─────────── ─────────── 15
Germline   hMu     CCCCTCGTCT  CCTGTGAGAA  TTCCCCGTCG  GATACGAGCA  GCGTGGCCGT  77
                   ─────────────────────── hμ ───────────────────▶
```

FIG.12B

```
Germline B3        GACATCGTGA TGACCCAGTC TCCAGACTCC CTGGCTGTGT CTCTGGGCGA
Hybridoma D5 1.4   ────────── ────────── ────────── ────────── ──────────
Germline JK3       ────────── ────────── ────────── ────────── ──────────
Germline CK        ────────── ────────── ────────── ────────── ──────────

┌──────────── CDR1 ────────────┐
Germline B3        GAGGGCCACC ATCAACTGCA AGTCCAGCCA GAGTGTTTT[A] TACA[GC]TCCA
Hybridoma D5 1.4   ──────ACC ATCAAGTGCA AGTCCAGCCA GAGTGTTTT[G] TACA[CT]TCCA
Germline JK3       ────────── ────────── ────────── ────────── ──────────
Germline CK        ────────── ────────── ────────── ────────── ──────────
                                    ◄──────────────── B3 ────────────

Germline B3        [A]CAATAAGAA CTACTTAGCT TGGTACCAGC AGAAACCAGG ACAGCCTCCT
Hybridoma D5 1.4   [G]CAATAAGAA CTACTTAGCT TGGTACCAGC AGAAACCAGG ACAGCCTCCT
Germline JK3       ────────── ────────── ────────── ────────── ──────────
Germline CK        ────────── ────────── ────────── ────────── ──────────
                   ──────────────────── B3 ────────────────────────────►

┌──────────── CDR2 ────────────┐
Germline B3        AA[GCTG]CTCA TTTACTGGGC ATCTACCCGG GAATCCGGGG TCCCTGACCG
Hybridoma D5 1.4   AA[ACTA]CTCA TTTACTGGGC ATCTACCCGG GAATCCGGGG TCCCTGACCG
Germline JK3       ────────── ────────── ────────── ────────── ──────────
Germline CK        ────────── ────────── ────────── ────────── ──────────
                   ──────────────────── B3 ────────────────────────────►

Germline B3        ATTCAGTGGC AGCGGGTCTG GGACAGATTT CACTCTCACC ATC[A]GCAGCC
Hybridoma D5 1.4   ATTCAGTGGC AGCGGGTCTG GGACAGATTT CACTCTCACC ATC[C]GCAGCC
Germline JK3       ────────── ────────── ────────── ────────── ──────────
Germline CK        ────────── ────────── ────────── ────────── ──────────
                   ──────────────────── B3 ────────────────────────────►

Germline B3        TGCAGGCTGA AGATGTGGCA GTTTATTACT GTCAGCAATA TTAT[AGTACT]
Hybridoma D5 1.4   TGCAGGCTGA AGATGTGGCA GTTTATTACT GTCAGCAATA TTAT[ACTATT]
Germline JK3       ────────── ────────── ────────── ────────── ──────────
Germline CK        ────────── ────────── ────────── ────────── ──────────
                   ──────────────────── B3 ────────────────────────────►

Germline B3        CC──────── ────────── ────────── ────────── ──────────
Hybridoma D5 1.4   CCATTCAATT TCGGCCCTGG GACCAGAGTG GATATCAAAC GAACTGTGGC
Germline JK3       ──ATTCACTT TCGGCCCTGG GACCAAAGTG GATATCAAAC ──────────
Germline CK        ────────── ────────── ────────── ────────── GAACTGTGGC
                   ──►│◄──────────── JK3 ────────────►│◄── CK ──
```

FIG. 13A

```
Germline B3        ─────────  ─────────  ─────────  ─────────  ─────────
Hybridoma D5 1.4   TGCACCATCT GTCTTCATCT TCCCGCCATC TGATGAGCAG TTGAAATCTG
Germline JK3       ─────────  ─────────  ─────────  ─────────  ─────────
Germline CK        TGCACCATCT GTCTTCATCT TCCCGCCATC TGATGAGCAG TTGAAATCTG
                   ─────────────────── CK ───────────────────▶

Germline B3        ─────────  ─────────  ─────────  ─────────  ─────────
Hybridoma D5 1.4   GAACTGCCTC TGTTGTGTGC CTGCTGAATA ACTTCTATCC CAGAGAGGCC
Germline JK3       ─────────  ─────────  ─────────  ─────────  ─────────
Germline CK        GAACTGCCTC TGTTGTGTGC CTGCTGAATA ACTTCTATCC CAGAGAGGCC
                   ─────────────────── CK ───────────────────▶

Germline B3        ─────────  ─────────  ─────────  ─────────  ─────────
Hybridoma D5 1.4   AAAGTACAGT GGAAGGTGGA TAACGCCCTC CAATCGGGTT GGGGAAAAA
Germline JK3       ─────────  ─────────  ─────────  ─────────  ─────────
Germline CK        AAAGTACAGT GGAAGGTGGA TAACGCCCTC CAATCGGGT- ─────────
                   ─────────────────── CK ───────────────────▶
```

FIG.13B

[CCTGTCCCTCACCTGCGCTGTCTATGGTGGGTCCTTCAGTGGTTACTACTGGAGCTGGATCCGCC
AGCCCCCAGGGAAGGGACTGGAGTGGATTGGGGAAATCAATCAAAGTGGAAGCACCAATTACAA
CCCGTCCCTCAAGAGTCGAGTCATCATATCAATAGACACGTCCAAGACCCAGTTCTCCCTGAAGT
TGAGCTCTGTGACCGCCGCGGACACGGCTGTGTATTACTGTGCGAGAGA][GACTCCCC][ATGCT
TTTGATATCTGGGGCCAAGGGACAATGGTCACCGTCTCTTCAG]CCTCCACCAAGGGCCCATCGG
TCTTCCCCCTGGCGCCCTGCTCCAGGAGCACCTCCGAGAGCACAGC(GC)GCCCTGGGCTGCCTG
GTCAAGGACTACTTCC

FIG. 16A

[CAGTCTCCATCCTCCCTGTCTGCATCTGTAGGCGACAGAGTCACCATCACTTGCCAGGCGAGTC
AGGACATTAGTAAGTTTTTAAGTTGGTTTCAACAGAAACCAGGGAAAGCCCCTAAACTCCTGATC
TACGGTACATCCTATTTGGAAACCGGGGTCCCATCAAGTTTCAGTGGAAGTGGATCTGGGACAGA
TTTTACTCTCACCATCAGCAGCCTGCAGCCTGAAGATGTTGCAACATATTTCTGTAACAGNATG
ATGATCTCCC][ATACACTTTCGGCCCTGGGACCAAAGTGGATATCAAAC]GAACTGTGGCTGCAC
CATCTGTCTTCATCTTCCCGCCATCTGATGAGCAGTTGAAATCTGGAACTGCCTCTGTTGTGCC
TGCTGAATAACTTCTATCCCAGAGAGGCCAAAGTACAGTGGAAGGTGGATAACGCCC

FIG. 16B

[AGGTCCCTGAGACTCTCCTGTGCAGCCTCTGGATTCACCTTCAGTAGCTATGGCATGCACTGGNT
CCGCCAGGCTCCAGGCAAGGGGCTGGAGTGGGTGGCAGAAATATCATATGATGGAAGTAATAAA
TACTATGTAGACTCCGTGAAGGGCCGACTCACCATCTCCAGAGACAATTCCAAGAACACGCTGT
ATCTGCAAATGAACAGCCTGAGAGCTGAGGACACGGCTGTGTATTACTGTGCGAGAGA][CCGAC
TGGGGAT][CTTTGACTACTGGGGCCAGGGAACCCTGGTCACCGTCTCCTCAG]CCTCCACCAAGG
GCCCATCGGTCTTCCCCCTGGCGCCCTGCTCCAGGAGCACCTCCGAGAGCACAGC(GC)GGCCCT
GGGCTGCCTGGTCCAAGGACTACTTCCCCCGAACCGGTGACGGTGTCGTGGAACTCAGGCGCTC
TGACCAG

FIG. 16C

[CTGACNCAGTCTCCAGACTCCCTGGCTGTGTCTCTGGGCGAGAGGGCCACCATCAACTGCAAGT
CCAGCCAGAGTGTTTTATACATCTCCAACAATAAAACTACTTAGCTTGGTACCAGCAGAAACCA
GGACAGTCTCCTAAACTGCTCATTTACTGGGCATCTACCCGGAAATCCGGGGTCCCTGACCGATT
CAGTGGCAGCGGGTCTGGGACAGATTTCACTCTCACCATCAGCAGCCTGCAGGCTGAAGATGTG
GCAGTTTATTACTGTCAACAGTATTATGATACTCC][ATTCACTTTCGGCCCTGGGACCAAAGTGG
ATATCAAAC]GAACTGTGGCTGCACCATCTGTCTTCATCTTCCCGCCATCTGATGAGCAGTTGAAA
TCTGGAACTGCCTCTGTTGTGTGCCTGCTGAATAACTTCTATCCCAGAGAGGCCAAAGTACAGTG
GAAGGTGGNTAACGCCCCA

FIG. 16D

[TCCCTCACCTGCGCTGTCTATGGTGGGTCCTTCAGTGGTTACTACTGGACCTGGATCCGCCAGCC
CCCAGGGAAGGGGCTGGAGTGGATTGGGGAAATCATTCATCATGGAAACACCAACTACAACCCG
TCCCTCAAGAGTCGAGTCTCCATATCAGTTGACACGTCCAAGAACCAGTTCTCCCTGACACTGAG
CTCTGTGACCGCCGCGGACACGGCTGTGTATTACTGTGCGAGAGG][GGGAGCAGTGGCTGCG][T
TTGACTACTGGGGCCAGGGAACCCTGGTCACCGTCTCCTCAG]CCTCCACCAAGGGCCCATCGGT
CTTCCCCCTGGCGCCCTGCTCCAGGAGCACCTCCGAGAGCACAGC(GC)GGCCCTGGGCTGCCTG
GTCAAGGACTACTTCCCCCGAACCGGTGACGGTGTCGTGGAACTCAGGCGCTCTGACCAGCGGC
GTGCACACCTTCCCA

FIG. 16E

[TGACCCAGTCTCCATCCTCCCTGTCTGCATCTGTAGGAGACAGAGTCACCATCACTTGCCAGGC
GAGTCAGGACATTAGTAACTATTTAAATTGGTATCAACAGAAAGCAGGGAAAGCCCCTAAGGTCC
TGATCTACGCTGCATCCAATTTGGAAGCAGGGGTCCCATCAAGGTTCAGTGGAAGTGGATCTGGG
ACAGATTTTACTTTCACCATCAGCAGCCTGCAGCCTGAAGATATTGCAACATATTATTGTCAACA
CTATGATAATCT]A[CTCACTTTCGGCGGAGGGACCAAGGTAGAGATCAAAC]GAACTGTGGCTGC
ACCATCTGTCTTCATCTTCCCGCCATCTGATGAGCAGTTGAAATCTGGACTGCCTCTGTTGTGTG
CCTGCTGAATAACTTCTATCCCAGAGAGGCCAAAGTACAGTGGAAGGTGG

FIG. 16F

AGTCTCTGAAGATCTCCTGTAAGGGTTCTGGATACAGCTTTACCAGCTACTGGATCGGCTGGGTG

CGCCAGATGCCCGGGAAAGGCCTGGAGTGGATGGGGATCATCTATCCTGGTGACTCTGATACCA

GATACAGCCCGTCCTTCCAAGGCCAGGTCACCATCTCAGCCGACAAGTCCATCAGCACCGCCTA

CCTGCAGTGGAGCAGCCTGAAGGCCTCGGACACCGCCATGTATTACTGTGCGAGACA][GGACGG

TG][ACTCCTTTGACTACTGGGGCCAGGGAACCCTGGTCACCGTCTCCTCAG]CCTCCACCAAGGG

CCCATCGGTCTTCCCCCTGGCGCCCTGCTCCAGGAGCACCTCCGAGAGCACAGC(GC)GGCCCTG

GGCTGCCTGGTCCAAGGACTACTTCCCCCGAACCGGTGACGGTGTCGTGGAACTCAGGCGCTCT

GACCAGCGGCGTGCACACCTTCCCACTGCCA

FIG. 16G

TGTCTGCATCTATTGGAGACAGAGTCACCATCACTTGCCGGGCAAGTCAGAGCATTAGCAACTA

TTTAAATTGGTATCAGCAGAAACCAGGGCAAAGCCCCTAAGTTCCTGATCTATGGTGCATCCAGT

TTGGAAAGTGGGGTCCCATCANGGTTCAGTGGCAGTGGATCTGGGACAGATTTCACTCTCACCAT

CAGCAGCCTGCAACCTGNGGATTTTGCAACTTACTACTGTCAACAGAGTTACAGTAACCC]T[CTC

ACTTTCGGCGGNGGGACCAANGTGGAGATCAAAC]GAACTGTGGCTGCACCATCTGTCTTCATCT

TCCCGCCATCTGATGAGCAGTTGAAATCTGGAACTGCCTCTGTTGTGTGCCTGCTGAATAACTTCT

ATCCCAGAGAGGCCAAAGTACA

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
      (A) LENGTH: 259 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:1:

```
AGACCCTCTC ACTCACCTGT GCCATCTCCG GGGACAGTGT CTCTAGCAAC AGTGCTGCTT      60

GGAACTGGAT CAGGCAGTCC CCATCGAGAG GCCTTGAGTG GCTGGGAAGG ACATACTACA     120

GGTCCAAGTG GTATAATGAT TATGCAGTAT CTGTGAAAAG TCGAATAACC ATCAACCCAG     180

ACACATCCAA GAACCAGTTC TCCCTGCAGC TGAACTCTGT GACTCCCGAG GACACGGCTG     240

TGTATTACTG TGCAAGAGA                                                  259
```

(2) INFORMATION FOR SEQ ID NO:2:

(i) SEQUENCE CHARACTERISTICS:
      (A) LENGTH: 400 base pairs (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:2:

```
AGACCCTCTC ACTCACCTGT GCCATCTCCG GGGACAGTGT CTCTAGCGAC AGTGCTGCTT      60

GGAACTGGAT CAGGCAGTCC CCATCGAGAG GCCTTGAGTG GCTGGGAAGG ACATACTACA     120

GGTCCAAGTG GTATAATGAT TATGCAGTTT CTGTGAAAAG TCGAATAACC ATCAACCCAG     180

ACACATCCAA GAACCAGTTC TCCCTGCAGC TGAACTCTGT GACTCCCGAG GACACGGCTG     240

TGTATTACTG TGCAAGAGAT ATAGCAGTGG CTGGCGTCCT CTTTGACTGC TGGGGCCAGG     300

GAACCCTGGT CACCGTCTCC TCAGGGAGTG CATCCGCCCC AACCCTTTTC CCCCTCGTCT     360

CCTGTGAGAA TTCCCCGTCG GATACGAGCA GCGTGGCCGT                           400
```

(2) INFORMATION FOR SEQ ID NO:3:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

```
CTTGACTAGC TGGGGCCAAG GAACCCTGGT CACCGTCTCC TCA                        43
```

(2) INFORMATION FOR SEQ ID NO:4:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

```
TATAGCAGCA GCTGG                                                       15
```

(2) INFORMATION FOR SEQ ID NO:5:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

```
GGGAGTGCAT CCGCCCCAAC CCTTTTCCCC CTCGTCTCCT GTGAGAATTC CCCGTCGGAT      60

ACGAGCAGCG TGGCCGT                                                     77
```

(2) INFORMATION FOR SEQ ID NO:6:

(i) SEQUENCE CHARACTERISTICS:
        (A) LENGTH: 302 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

```
GACATCGTGA TGACCCAGTC TCCAGACTCC CTGGCTGTGT CTCTGGGCGA GAGGGCCACC    60
ATCAACTGCA AGTCCAGCCA GAGTGTTTTA TACAGCTCCA ACAATAAGAA CTACTTAGCT   120
TGGTACCAGC AGAAACCAGG ACAGCCTCCT AAGCTGCTCA TTTACTGGGC ATCTACCCGG   180
GAATCCGGGG TCCCTGACCG ATTCAGTGGC AGCGGGTCTG GGACAGATTT CACTCTCACC   240
ATCAGCAGCC TGCAGGCTGA AGATGTGGCA GTTTATTACT GTCAGCAATA TTATAGTACT   300
CC                                                                  302
```

(2) INFORMATION FOR SEQ ID NO:7:

(i) SEQUENCE CHARACTERISTICS:
        (A) LENGTH: 442 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

```
ACCATCAAGT GCAAGTCCAG CCAGAGTGTT TTGTACACTT CCAGCAATAA GAACTACTTA    60
GCTTGGTACC AGCAGAAACC AGGACAGCCT CCTAAACTAC TCATTTACTG GGCATCTACC   120
CGGGAATCCG GGGTCCCTGA CCGATTCAGT GGCAGCGGGT CTGGGACAGA TTTCACTCTC   180
ACCATCCGCA GCCTGCAGGC TGAAGATGTG GCAGTTTATT ACTGTCAGCA ATATTATACT   240
ATTCCATTCA ATTTCGGCCC TGGGACCAGA GTGGATATCA AACGAACTGT GGCTGCACCA   300
TCTGTCTTCA TCTTCCCGCC ATCTGATGAG CAGTTGAAAT CTGGAACTGC CTCTGTTGTG   360
TGCCTGCTGA ATAACTTCTA TCCCAGAGAG GCCAAAGTAC AGTGGAAGGT GGATAACGCC   420
CTCCAATCGG GTTGGGGAAA AA                                            442
```

(2) INFORMATION FOR SEQ ID NO:8:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

```
ATTCACTTTC GGCCCTGGGA CCAAAGTGGA TATCAAAC                            38
```

(2) INFORMATION FOR SEQ ID NO:9:

(i) SEQUENCE CHARACTERISTICS:
        (A) LENGTH: 149 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

```
GAACTGTGGC TGCACCATCT GTCTTCATCT TCCCGCCATC TGATGAGCAG TTGAAATCTG    60
GAACTGCCTC TGTTGTGTGC CTGCTGAATA ACTTCTATCC CAGAGAGGCC AAAGTACAGT   120
GGAAGGTGGA TAACGCCCTC CAATCGGGT                                     149
```

(2) INFORMATION FOR SEQ ID NO:10:

(i) SEQUENCE CHARACTERISTICS:
        (A) LENGTH: 399 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

| | | | | | |
|---|---|---|---|---|---|
| CCTGTCCCTC | ACCTGCGCTG | TCTATGGTGG | GTCCTTCAGT | GGTTACTACT | GGAGCTGGAT | 60 |
| CCGCCAGCCC | CCAGGGAAGG | GACTGGAGTG | GATTGGGAA | ATCAATCAAA | GTGGAAGCAC | 120 |
| CAATTACAAC | CCGTCCCTCA | AGAGTCGAGT | CATCATATCA | ATAGACACGT | CCAAGACCCA | 180 |
| GTTCTCCCTG | AAGTTGAGCT | CTGTGACCGC | CGCGGACACG | GCTGTGTATT | ACTGTGCGAG | 240 |
| AGAGACTCCC | CATGCTTTTG | ATATCTGGGG | CCAAGGGACA | ATGGTCACCG | TCTCTTCAGC | 300 |
| CTCCACCAAG | GGCCCATCGG | TCTTCCCCCT | GGCGCCCTGC | TCCAGGAGCA | CCTCCGAGAG | 360 |
| CACAGCGCGC | CCTGGGCTGC | CTGGTCAAGG | ACTACTTCC | | | 399 |

(2) INFORMATION FOR SEQ ID NO:11:

(i) SEQUENCE CHARACTERISTICS:
        (A) LENGTH: 444 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

CAGTCTCCAT CCTCCCTGTC TGCATCTGTA GGCGACAGAG TCACCATCAC TTGCCAGGCG    60
AGTCAGGACA TTAGTAAGTT TTTAAGTTGG TTTCAACAGA AACCAGGGAA AGCCCCTAAA   120
CTCCTGATCT ACGGTACATC CTATTTGGAA ACCGGGGTCC CATCAAGTTT CAGTGGAAGT   180
GGATCTGGGA CAGATTTTAC TCTCACCATC AGCAGCCTGC AGCCTGAAGA TGTTGCAACA   240
TATTTCTGTA ACAGNATGAT GATCTCCCAT ACACTTTCGG CCCTGGGACC AAAGTGGATA   300
TCAAACGAAC TGTGGCTGCA CCATCTGTCT TCATCTTCCC GCCATCTGAT GAGCAGTTGA   360
AATCTGGAAC TGCCTCTGTT GTGTGCCTGC TGAATAACTT CTATCCCAGA GAGGCCAAAG   420
TACAGTGGAA GGTGGATAAC GCCC                                         444

(2) INFORMATION FOR SEQ ID NO:12:

(i) SEQUENCE CHARACTERISTICS:
        (A) LENGTH: 453 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

AGGTCCCTGA GACTCTCCTG TGCAGCCTCT GGATTCACCT TCAGTAGCTA TGGCATGCAC    60
TGGNTCCGCC AGGCTCCAGG CAAGGGGCTG GAGTGGGTGG CAGAAAATATC ATATGATGGA   120
AGTAATAAAT ACTATGTAGA CTCCGTGAAG GGCCGACTCA CCATCTCCAG AGACAATTCC   180
AAGAACACGC TGTATCTGCA AATGAACAGC CTGAGAGCTG AGGACACGGC TGTGTATTAC   240
TGTGCGAGAG ACCGACTGGG GATCTTTGAC TACTGGGGCC AGGGAACCCT GGTCACCGTC   300
TCCTCAGCCT CCACCAAGGG CCCATCGGTC TTCCCCCTGG CGCCCTGCTC CAGGAGCACC   360

```
TCCGAGAGCA CAGCGCGGCC CTGGGCTGCC TGGTCCAAGG ACTACTTCCC CCGAACCGGT      420

GACGGTGTCG TGGAACTCAG GCGCTCTGAC CAG                                  453
```

(2) INFORMATION FOR SEQ ID NO:13:

(i) SEQUENCE CHARACTERISTICS:
        (A) LENGTH: 470 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

```
CTGACNCAGT CTCCAGACTC CCTGGCTGTG TCTCTGGGCG AGAGGGCCAC CATCAACTGC       60

AAGTCCAGCC AGAGTGTTTT ATACATCTCC AACAATAAAA CTACTTAGCT TGGTACCAGC      120

AGAAACCAGG ACAGTCTCCT AAACTGCTCA TTTACTGGGC ATCTACCCGG AAATCCGGGG      180

TCCCTGACCG ATTCAGTGGC AGCGGGTCTG GGACAGATTT CACTCTCACC ATCAGCAGCC      240

TGCAGGCTGA AGATGTGGCA GTTTATTACT GTCAACAGTA TTATGATACT CCATTCACTT      300

TCGGCCCTGG GACCAAAGTG GATATCAAAC GAACTGTGGC TGCACCATCT GTCTTCATCT      360

TCCCGCCATC TGATGAGCAG TTGAAATCTG GAACTGCCTC TGTTGTGTGC CTGCTGAATA      420

ACTTCTATCC CAGAGAGGCC AAAGTACAGT GGAAGGTGGN TAACGCCCCA                 470
```

(2) INFORMATION FOR SEQ ID NO:14:

(i) SEQUENCE CHARACTERISTICS:
        (A) LENGTH: 462 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

```
TCCCTCACCT GCGCTGTCTA TGGTGGGTCC TTCAGTGGTT ACTACTGGAC CTGGATCCGC       60

CAGCCCCCAG GGAAGGGGCT GGAGTGGATT GGGGAAATCA TTCATCATGG AAACACCAAC      120

TACAACCCGT CCCTCAAGAG TCGAGTCTCC ATATCAGTTG ACACGTCCAA GAACCAGTTC      180

TCCCTGACAC TGAGCTCTGT GACCGCCGCG GACACGGCTG TGTATTACTG TGCGAGAGGG      240

GGAGCAGTGG CTGCGTTTGA CTACTGGGGC CAGGGAACCC TGGTCACCGT CTCCTCAGCC      300

TCCACCAAGG GCCCATCGGT CTTCCCCCTG GCGCCCTGCT CCAGGAGCAC CTCCGAGAGC      360

ACAGCGCGGC CCTGGGCTGC CTGGTCAAGG ACTACTTCCC CCGAACCGGT GACGGTGTCG      420

TGGAACTCAG GCGCTCTGAC CAGCGGCGTG CACACCTTCC CA                        462
```

(2) INFORMATION FOR SEQ ID NO:15:

(i) SEQUENCE CHARACTERISTICS:
        (A) LENGTH: 437 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

```
TGACCCAGTC TCCATCCTCC CTGTCTGCAT CTGTAGGAGA CAGAGTCACC ATCACTTGCC       60

AGGCGAGTCA GGACATTAGT AACTATTTAA ATTGGTATCA ACAGAAAGCA GGGAAAGCCC      120
```

```
CTAAGGTCCT GATCTACGCT GCATCCAATT TGGAAGCAGG GGTCCCATCA AGGTTCAGTG        180

GAAGTGGATC TGGGACAGAT TTTACTTTCA CCATCAGCAG CCTGCAGCCT GAAGATATTG        240

CAACATATTA TTGTCAACAC TATGATAATC TACTCACTTT CGGCGGAGGG ACCAAGGTAG        300

AGATCAAACG AACTGTGGCT GCACCATCTG TCTTCATCTT CCCGCCATCT GATGAGCAGT        360

TGAAATCTGG ACTGCCTCTG TTGTGTGCCT GCTGAATAAC TTCTATCCCA GAGAGGCCAA        420

AGTACAGTGG AAGGTGG                                                      437

(2) INFORMATION FOR SEQ ID NO:16:

(i) SEQUENCE CHARACTERISTICS:
        (A) LENGTH: 477 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

AGTCTCTGAA GATCTCCTGT AAGGGTTCTG GATACAGCTT TACCAGCTAC TGGATCGGCT         60

GGGTGCGCCA GATGCCCGGG AAAGGCCTGG AGTGGATGGG GATCATCTAT CCTGGTGACT        120

CTGATACCAG ATACAGCCCG TCCTTCCAAG GCCAGGTCAC CATCTCAGCC GACAAGTCCA        180

TCAGCACCGC CTACCTGCAG TGGAGCAGCC TGAAGGCCTC GGACACCGCC ATGTATTACT        240

GTGCGAGACA GGACGGTGAC TCCTTTGACT ACTGGGGCCA GGGAACCCTG GTCACCGTCT        300

CCTCAGCCTC CACCAAGGGC CCATCGGTCT TCCCCCTGGC GCCCTGCTCC AGGAGCACCT        360

CCGAGAGCAC AGCGCGGCCC TGGGCTGCCT GGTCCAAGGA CTACTTCCCC CGAACCGGTG        420

ACGGTGTCGT GGAACTCAGG CGCTCTGACC AGCGGCGTGC ACACCTTCCC ACTGCCA          477

(2) INFORMATION FOR SEQ ID NO:17:

(i) SEQUENCE CHARACTERISTICS:
        (A) LENGTH: 410 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

TGTCTGCATC TATTGGAGAC AGAGTCACCA TCACTTGCCG GGCAAGTCAG AGCATTAGCA         60

ACTATTTAAA TTGGTATCAG CAGAAACCAG GGCAAAGCCC CTAAGTTCCT GATCTATGGT        120

GCATCCAGTT TGGAAAGTGG GGTCCCATCA NGGTTCAGTG GCAGTGGATC TGGGACAGAT        180

TTCACTCTCA CCATCAGCAG CCTGCAACCT GNGGATTTTG CAACTTACTA CTGTCAACAG        240

AGTTACAGTA ACCCTCTCAC TTTCGGCGGN GGGACCAANG TGGAGATCAA ACGAACTGTG        300

GCTGCACCAT CTGTCTTCAT CTTCCCGCCA TCTGATGAGC AGTTGAAATC TGGAACTGCC        360

TCTGTTGTGT GCCTGCTGAA TAACTTCTAT CCCAGAGAGG CCAAAGTACA                   410

(2) INFORMATION FOR SEQ ID NO:18:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA
```

```
         (xi) SEQUENCE DESCRIPTION: SEQ ID NO:18:

CTCTGTGACA CTCTCCTGGG AGTT                                                        24

(2) INFORMATION FOR SEQ ID NO:19:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:19:

GAAACGACAC TCACGCAGTC TCCAGC                                                      26

(2) INFORMATION FOR SEQ ID NO:20:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:20:

TTTTCTTTGT TGCCGTTGGG GTGC                                                        24

(2) INFORMATION FOR SEQ ID NO:21:

(i) SEQUENCE CHARACTERISTICS:
          (A) LENGTH: 28 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:21:

GCTGAGGGAG TAGAGTCCTG AGGACTGT                                                    28
```

HUMAN ANTIBODIES DERIVED FROM IMMUNIZED XENOMICE

CROSS REFERENCE TO RELATED APPLICATIONS

The present application claims benefit under 35 U.S.C. § 120 as a continuation-in-part of U.S. patent application Ser. No. 08/430,938, filed Apr. 27, 1995, now abandoned, which is a continuation-in-part of U.S. patent application Ser. Nos. 08/234,143, 08/112,848, 08/031,801, 07/919,297, 07/610,515, and 07/466,008 (filed Apr. 28, 1994, now abandoned Aug. 27, 1993, now abandoned; Mar. 15, 1993, pending; Jul. 24, 1992, now abandoned; Nov. 8, 1990 now abandoned; and Jan. 12, 1990, now abandoned; respectively). The present application also claims benefit under 35 U.S.C. § 120 to A C-I-P PCT/US96/05928, filed Apr. 29, 1996. The disclosures of each of the aforementioned applications are hereby incorporated by reference in their entirety.

TECHNICAL FIELD

The invention relates to the field of immunology, and in particular to the production of antibodies. More specifically, it concerns producing such antibodies by a process which includes the step of immunizing a transgenic animal with an antigen to which antibodies are desired. The transgenic animal has been modified so as to produce human, as opposed to endogenous, antibodies.

BACKGROUND ART

PCT application WO 94/02602, published 3 Feb. 1994 and incorporated herein by reference, describes in detail the production of transgenic nonhuman animals which are modified so as to produce fully human antibodies rather than endogenous antibodies in response to antigenic challenge. Briefly, the endogenous loci encoding the heavy and light immunoglobulin chains are incapacitated in the transgenic hosts and loci encoding human heavy and light chain proteins are inserted into the genome. In general, the animal which provides all the desired modifications is obtained by cross breeding intermediate animals containing fewer than the full complement of modifications. The preferred embodiment of nonhuman animal described in the specification is a mouse. Thus, mice, specifically, are described which, when administered immunogens, produce antibodies with human variable regions, including fully human antibodies, rather than murine antibodies that are immunospecific for these antigens.

The availability of such transgenic animals makes possible new approaches to the production of fully human antibodies. Antibodies with various immunospecificities are desirable for therapeutic and diagnostic use. Those antibodies intended for human therapeutic and in vivo diagnostic use, in particular, have been problematic because prior art sources for such antibodies resulted in immunoglobulins bearing the characteristic structures of antibodies produced by nonhuman hosts. Such antibodies tend to be immunogenic when used in humans.

The availability of the nonhuman, immunogen responsive transgenic animals described in the above-referenced wo 94/02602 make possible convenient production of human antibodies without the necessity of employing human hosts.

DISCLOSURE OF THE INVENTION

The invention is directed to methods to produce human antibodies by a process wherein at least one step of the process includes immunizing a transgenic nonhuman animal with the desired antigen. The modified animal fails to produce endogenous antibodies, but instead produces B-cells which secrete fully human immunoglobulins. The antibodies produced can be obtained from the animal directly or from immortalized B-cells derived from the animal. Alternatively, the genes encoding the immunoglobulins with human variable regions can be recovered and expressed to obtain the antibodies directly or modified to obtain analogs of antibodies such as, for example, single chain $F_v$ molecules.

Thus, in one aspect, the invention is directed to a method to produce a fully human immunoglobulin to a specific antigen or to produce an analog of said immunoglobulin by a process which comprises immunizing a nonhuman animal with the antigen under conditions that stimulate an immune response. The nonhuman animal is characterized by being substantially incapable of producing endogenous heavy or light immunoglobulin chain, but capable of producing immunoglobulins with both human variable and constant regions. In the resulting immune response, the animal produces B cells which secrete immunoglobulins that are fully human and specific for the antigen. The human immunoglobulin of desired specificity can be directly recovered from the animal, for example, from the serum, or primary B cells can be obtained from the animal and immortalized. The immortalized B cells can be used directly as the source of human antibodies or, alternatively, the genes encoding the antibodies can be prepared from the immortalized B cells or from primary B cells of the blood or lymphoid tissue (spleen, tonsils, lymph nodes, bone marrow) of the immunized animal and expressed in recombinant hosts, with or without modifications, to produce the immunoglobulin or its analogs. In addition, the genes encoding the repertoire of immunoglobulins produced by the immunized animal can be used to generate a library of immunoglobulins to permit screening for those variable regions which provide the desired affinity. Clones from the library which have the desired characteristics can then be used as a source of nucleotide sequences encoding the desired variable regions for further manipulation to generate antibodies or analogs with these characteristics using standard recombinant techniques.

In another aspect, the invention relates to an immortalized nonhuman B cell line derived from the above described animal. In still another aspect, the invention is directed to a recombinant host cell which is modified to contain the gene encoding either the human immunoglobulin with the desired specificity, or an analog thereof which exhibits the same specificity.

In still other aspects, the invention is directed to antibodies or antibody analogs prepared by the above-described methods and to recombinant materials for their production.

In still other aspects, the invention is directed to antibodies which are immunospecific with respect to particular antigens set forth herein and to analogs which are similarly immunospecific, as well as to the recombinant materials useful to production of these antibodies.

BRIEF DESCRIPTION OF THE DRAWINGS

FIG. 12(A&B) DNA sequence (SEQ ID NO:2) of the heavy chain of anti tetanus toxin monoclonal antibody D5.1.4 (a subclone of D5.1). Mutations from germline are boxed. Germline VH6, (SEQ ID NO: 1); Germline JH4, (SEQ ID NO: 3); Germline D(N1), (SEQ ID NO: 4); Germline hMu, (SEQ ID NO: 5).

FIG. 13(A&B) DNA sequence (SEQ ID NO:7) of the kappa light chain of anti-tetanus toxin monoclonal antibody D5.1.4. Mutations from germline are boxed. Germline B3, (SEQ ID NO: 6); Germline JK3, (SEQ ID NO: 8); Germline CK, (SEQ ID NO: 9).

FIG. 16 (A–H) DNA sequences of the heavy chain and kappa light chain of the anti-IL-8 antibodies FIG. 16A, D1.1 heavy chain (SEQ ID NO: 10); FIG. 16B, D1.1 light chain (SEQ ID NO: 11); FIG. 16C, K2.2 heavy chain (SEQ ID NO: 12); FIG. 16D, K2.2 light chain (SEQ ID NO: 13); FIG. 16E, K4.2 heavy chain (SEQ ID NO: 14); FIG. 16F, K4.2 light chain (SEQ ID NO: 15); FIG. 16G, K4.3 heavy chain (SEQ ID NO: 16); FIG. 16H, K4.3 light chain (SEQ ID NO: 17).

MODES OF CARRYING OUT THE INVENTION

In general, the methods of the invention include administering an antigen for which human forms of immunospecific reagents are desired to a transgenic nonhuman animal which has been modified genetically so as to be capable of producing human, but not endogenous, antibodies. Typically, the animal has been modified to disable the endogenous heavy and/or kappa light chain loci in its genome, so that these endogenous loci are incapable of the rearrangement required to generate genes encoding immunoglobulins in response to an antigen. In addition, the animal will have been provided, stably, in its genome, at least one human heavy chain locus and at least one human light chain locus so that in response to an administered antigen, the human loci can rearrange to provide genes encoding human variable regions immunospecific for the antigen.

Figure 1:
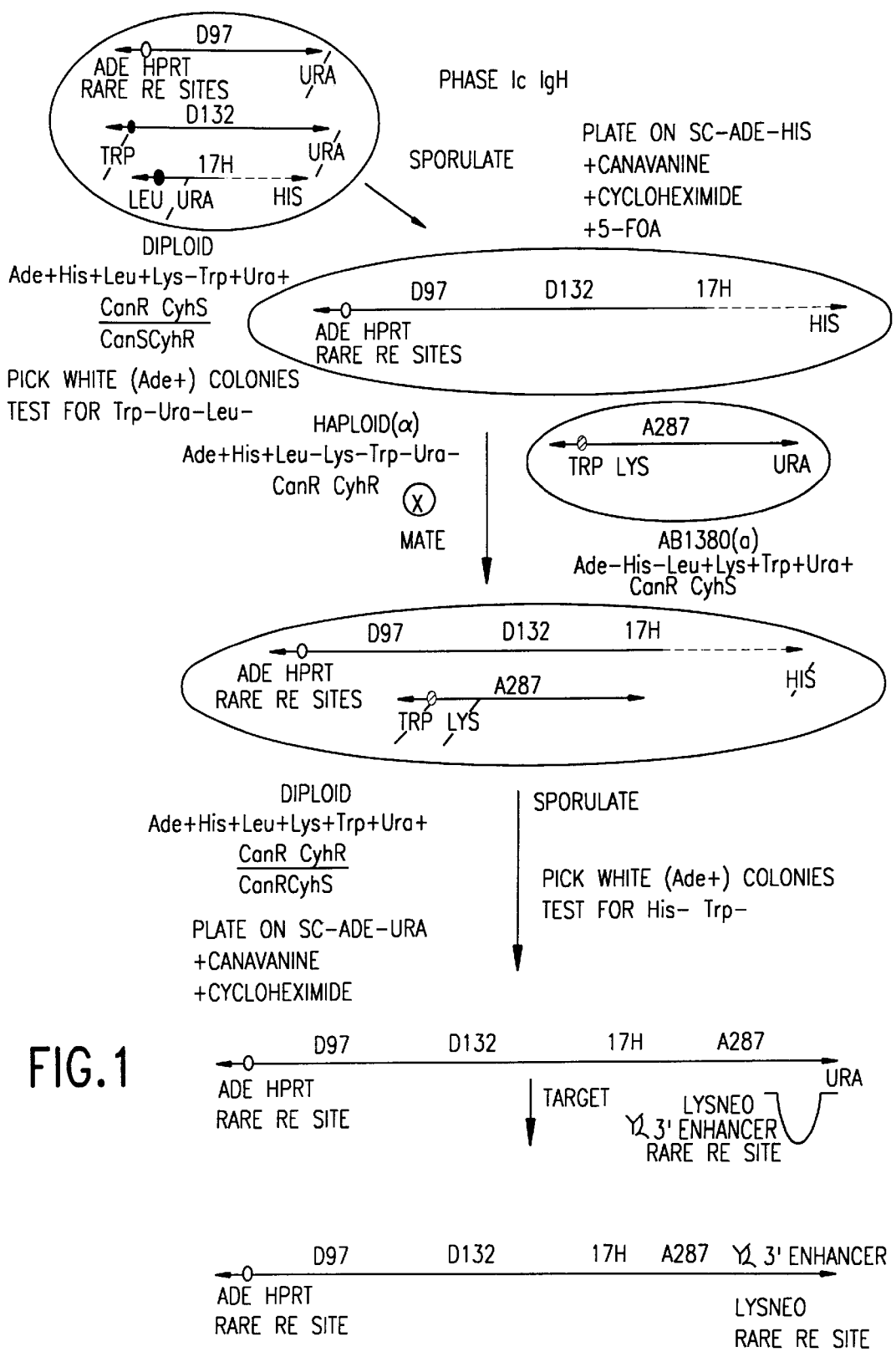
FIG. 1 is a schematic of the construction of the yH1C human heavy chain YAC.
Figure 2:
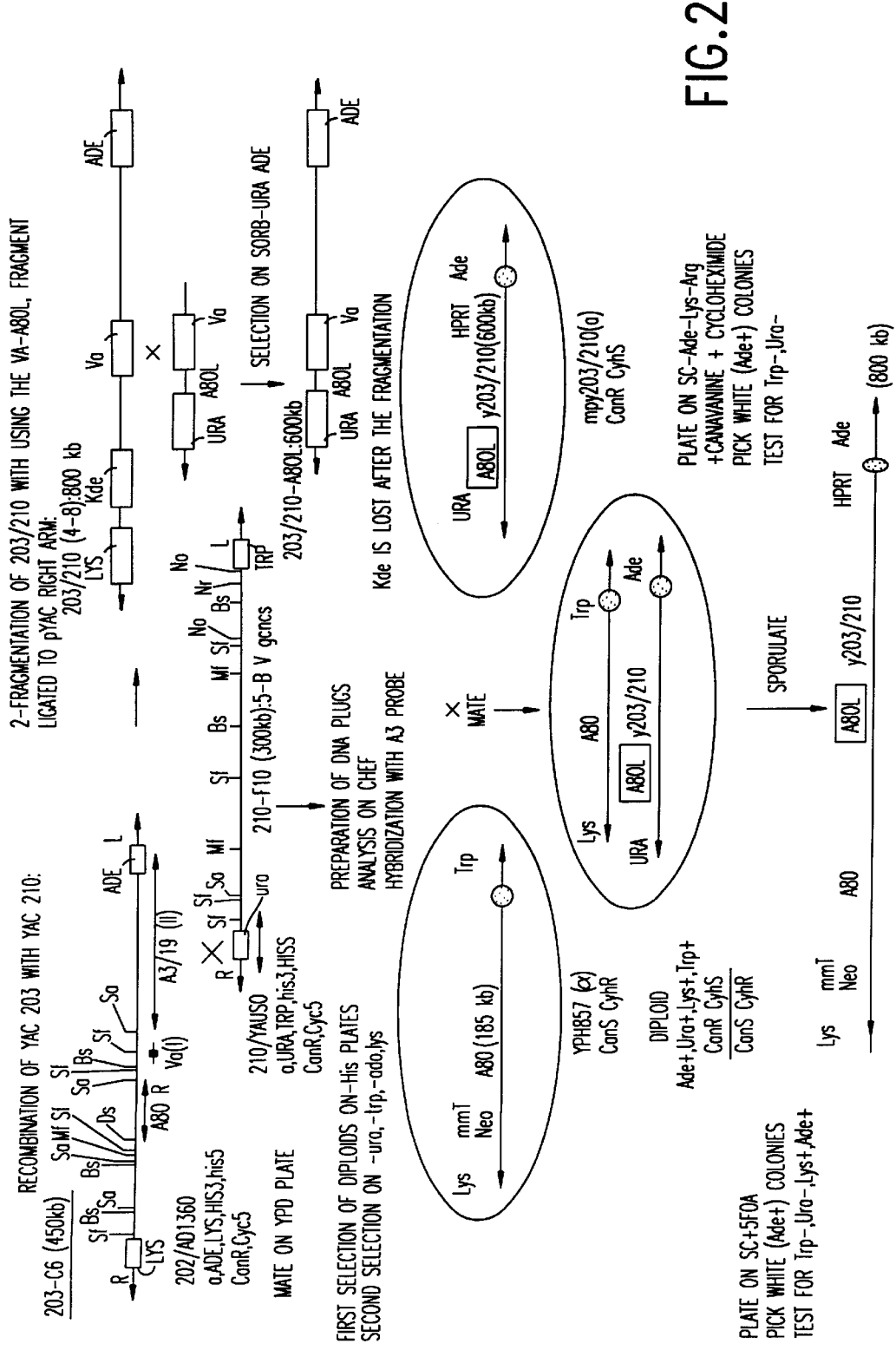
FIG. 2 is a schematic of the construction of the yK2 human kappa light chain YAC.

The details for constructing such an animal useful in the method of the invention are provided in the PCT application WO 94/02602 referenced above. Examples of YACs for the present invention can be found in, for example, Green et al. *Nature Genetics* 7:13–21 (1994). In a preferred embodiment of the XenoMouse™, the human heavy chain YAC, yH1C (1020 kb), and human light chain YAC, yK2 (880 kb) are used. yH1C is comprised of 870 kb of the human variable region, the entire D and $J_H$ region, human μ, δ, and γ2 constant regions and the mouse 3' enhancer. yK2 is comprised of 650 kb of the human kappa chain proximal variable region (Vκ), the entire Jκ region, and Cκ with its flanking sequences that contain the Kappa deleting element (κde). Both YACs also contain a human HPRT selectable marker on their YAC vector arm. Construction of yH1C and yK2 was accomplished by methods well known in the art. In brief, YAC clones bearing segments of the human immunoglobulin loci were identified by screening a YAC library (Calbertsen et al, *PNAS* 87:4256 (1990)) Overlapping clones were joined by recombination using standard techniques (Mendez et al. *Genomics* 26:294–307 (1995)). Details of the schemes for assembling yH1C and yK2 are shown in FIG. 1 and FIG. 2 respectively.

yK2 was constructed from the clones A80-C7, A210-F10 and A203-C6 from the Olson library, disclosed in, for example, Burke et al., *Science* 236:806–812 (1987), Brownstein et al., *Science* 244:1348–1351 (1989), and Burke et al., *Methods in Enzymology* 194:251–270 (1991).

For production of the desired antibodies, the first step is administration of the antigen. Techniques for such administration are conventional and involve suitable immunization protocols and formulations which will depend on the nature of the antigen per se. It may be necessary to provide the antigen with a carrier to enhance its immunogenicity and/or to include formulations which contain adjuvants and/or to administer multiple injections and/or to vary the route of the immunization, and the like. Such techniques are standard and optimization of them will depend on the characteristics of the particular antigen for which immunospecific reagents are desired.

As used herein, the term "immunospecific reagents" includes immunoglobulins and their analogs. The term "analogs" has a specific meaning in this context. It refers to moieties that contain the fully human portions of the immunoglobulin which account for its immunospecificity. In particular, complementarity determining regions (CDRs) are required, along with sufficient portions of the framework (Frs) to result in the appropriate three dimensional conformation. Typical immunospecific analogs of antibodies include F(abl")$_2$, Fab', and Fab regions. Modified forms of the variable regions to obtain, for example, single chain $F_v$ analogs with the appropriate immunospecificity are known. A review of such $F_v$ construction is found, for example, in Huston et al., *Methods in Enzymology* 203:46–63 (1991). The construction of antibody analogs with multiple immunospecificities is also possible by coupling the variable regions from one antibody to those of second antibody.

The variable regions with fully human characteristics can also be coupled to a variety of additional substances which can provide toxicity, biological functionality, alternative binding specificities and the like. The moieties including the fully human variable regions produced by the methods of the invention include single-chain fusion proteins, molecules coupled by covalent methods other than those involving peptide linkages, and aggregated molecules. Examples of analogs which include variable regions coupled to additional molecules covalently or noncovalently include those in the following nonlimiting illustrative list. Traunecker, A. et al. *Int. J. Cancer Supp* (1992) *Supp* 7:51–52 describe the bispecific reagent janusin in which the $F_v$ region directed to CD3 is coupled to soluble CD4 or to other ligands such as OVCA and IL-7. Similarly, the fully human variable regions produced by the method of the invention can be constructed into $F_v$ molecules and coupled to alternative ligands such as those illustrated in the cited article. Higgins, P. J. et al *J.Infect Disease* (1992) 166:198–202 described a heteroconjugate antibody composed of OKT3 cross-linked to an antibody directed to a specific sequence in the V3 region of GP120. Such heteroconjugate antibodies can also be constructed using at least the human variable regions contained in the immunoglobulins produced by the invention methods. Additional examples of bispecific antibodies include those described by Fanger, M. W. et al. *Cancer Treat Res* (1993) 68:181–194 and by Fanger, M. W. et al. *Crit Rev Immunol* (1992) 12:101–124. Conjugates that are immunotoxins including conventional antibodies have been widely described in the art. The toxins may be coupled to the antibodies by conventional coupling techniques or immunotoxins containing protein toxin portions can be produced as fusion proteins. The analogs of the present invention can be used in a corresponding way to obtain such immunotoxins. Illustrative of such immunotoxins are those described by Byers, B. S. et al. *Seminars Cell Biol* (1991) 2:59–70 and by Fanger, M. W. et al. *Immunol Today* (1991) 12:51–54.

It will also be noted that some of the immunoglobulins and analogs of the invention will have agonist activity with respect to antigens for which they are immunospecific in the cases wherein the antigens perform signal transducing functions. Thus, a subset of antibodies or analogs prepared according to the methods of the invention which are immunospecific for, for example, a cell surface receptor, will be capable of eliciting a response from cells bearing this receptor corresponding to that elicited by the native ligand. Furthermore, antibodies or analogs which are immunospecific for substances mimicking transition states of chemical reactions will have catalytic activity. Hence, a subset of the antibodies and analogs of the invention will function as catalytic antibodies.

In short, the genes encoding the immunoglobulins produced by the transgenic animals of the invention can be retrieved and the nucleotide sequences encoding the fully human variable region can be manipulated according to known techniques to provide a variety of analogs such as those described above. In addition, the immunoglobulins themselves containing the human variable regions can be modified using standard coupling techniques to provide conjugates retaining immunospecific regions.

Thus, immunoglobulin "analogs" refers to the moieties which contain those portions of the antibodies of the invention which retain their human characteristics and their immunospecificity. These will retain sufficient human variable regions to provide the desired specificity.

It is predicted that the specificity of antibodies (i.e., the ability to generate antibodies to a wide spectrum of antigens and indeed to a wide spectrum of independent epitopes thereon) is dependent upon the variable region genes on the heavy chain ($V_H$) and kappa light chain ($V_K$) genome. The human heavy chain genome includes approximately 82 genes which encode variable regions of the human heavy chain of immunoglobulin molecules. In addition, the human light chain genome includes approximately 40 genes on its proximal end which encode variable regions of the human kappa light chain of immunoglobulin molecules. We have demonstrated that the specificity of antibodies can be enhanced through the inclusion of a plurality of genes encoding variable light and heavy chains.

In preferred embodiments, therefore, greater than 10% of $V_H$ and $V_K$ genes are utilized. More preferably, greater than 20%, 30%, 40%, 50%, 60% or even 70% or greater of $V_H$ and $V_K$ genes are utilized. In a preferred embodiment, constructs including 32 genes on the proximal region of the $V_K$ light chain genome are utilized and 66 genes on the $V_H$ portion of the genome are utilized. As will be appreciated, genes may be included either sequentially, i.e., in the order found in the human genome, or out of sequence, i.e., in an order other than that found in the human genome, or a combination thereof. Thus, by way of example, an entirely sequential portion of either the $V_H$ or $V_K$ genome can be utilized, or various V genes in either the $V_H$ or $V_K$ genome can be skipped while maintaining an overall sequential arrangement, or V genes within either the $V_H$ or $V_K$ genome can be reordered, and the like. In any case, it is expected and the results described herein demonstrate that the inclusion of a diverse array of genes from the $V_H$ and $V_K$ genome leads to enhanced antibody specificity and ultimately to enhanced antibody affinities.

With respect to affinities, antibody affinity rates and constants derived through utilization of plural $V_H$ and $V_K$ genes (i.e., the use of 32 genes on the proximal region of the $V_K$ light chain genome and 66 genes on the $V_H$ portion of the genome) results in association rates (Ka in $M^{-1}S^{-1}$) of greater than about $0.50 \times 10^{-6}$, preferably greater than $2.00 \times 10^{-6}$, and more preferably greater than about $4.00 \times 10^{-6}$; dissociation rates (kd in $S^{-1}$) of greater than about $1.00 \times 10^{-4}$, preferably greater than about $2.00 \times 10^{-4}$, and more preferably greater than about $4.00 \times 10^{-4}$; and dissociation constant (in M) of greater than about $1.00 \times 10^{-10}$, preferably greater than about $2.00 \times 10^{-10}$, and more preferably greater than about $4.00 \times 10^{-10}$.

As stated above, all of the methods of the invention include administering the appropriate antigen to the transgenic animal. The recovery or production of the antibodies themselves can be achieved in various ways.

First, and most straightforward, the polyclonal antibodies produced by the animal and secreted into the bloodstream can be recovered using known techniques. Purified forms of these antibodies can, of course, be readily prepared by standard purification techniques, preferably including affinity chromatography with Protein A, anti-immunoglobulin, or the antigen itself. In any case, in order to monitor the success of immunization, the antibody levels with respect to the antigen in serum will be monitored using standard techniques such as ELISA, RIA and the like.

For some applications only the variable regions of the antibodies are required. Treating the polyclonal antiserum with suitable reagents so as to generate Fab', Fab, or F(ab")$_2$ portions results in compositions retaining fully human characteristics. Such fragments are sufficient for use, for example, in immunodiagnostic procedures involving coupling the immunospecific portions of immunoglobulins to detecting reagents such as radioisotopes.

Alternatively, immunoglobulins and analogs with desired characteristics can be generated from immortalized B cells derived from the transgenic animals used in the method of the invention or from the rearranged genes provided by these animals in response to immunization.

Thus, as an alternative to harvesting the antibodies directly from the animal, the B cells can be obtained, typically from the spleen, but also, if desired, from the peripheral blood lymphocytes or lymph nodes and immortalized using any of a variety of techniques, most commonly using the fusion methods described by Kohler and Milstein Nature 245:495 (1975) The resulting hybridomas (or otherwise immortalized B cells) can then be cultured as single colonies and screened for secretion of antibodies of the desired specificity. As described above, the screen can also include a confirmation of the fully human character of the antibody. For example, as described in the examples below, a sandwich ELISA wherein the monoclonal in the hybridoma supernatant is bound both to antigen and to an antihuman constant region can be employed. After the appropriate hybridomas are selected, the desired antibodies can be recovered, again using conventional techniques. They can be prepared in quantity by culturing the immortalized B cells using conventional methods, either in vitro or in vivo to produce ascites fluid. Purification of the resulting monoclonal antibody preparations is less burdensome that in the case of serum since each immortalized colony will secrete only a single type of antibody. In any event, standard purification techniques to isolate the antibody from other proteins in the culture medium can be employed.

As an alternative to obtaining human immunoglobulins directly from the culture of immortalized B cells derived from the animal, the immortalized cells can be used as a source of rearranged heavy chain and light chain loci for subsequent expression and/or genetic manipulation. Rearranged antibody genes can be reverse transcribed from appropriate mRNAs to produce cDNA. If desired, the heavy chain constant region can be exchanged for that of a different isotype or eliminated altogether. The variable regions can be linked to encode single chain $F_v$ regions. Multiple $F_v$ regions can be linked to confer binding ability to more than one target or chimeric heavy and light chain combinations can be employed. Once the genetic material is available, design of analogs as described above which retain both their ability to bind the desired target, and their human characteristics, is straightforward.

Once the appropriate genetic material is obtained and, if desired, modified to encode an analog, the coding sequences, including those that encode, at a minimum, the variable regions of the human heavy and light chain, can be inserted into expression systems contained on vectors which can be transfected into standard recombinant host cells. As described below, a variety of such host cells may be used; for efficient processing, however, mammalian cells are preferred. Typical mammalian cell lines useful for this purpose include CHO cells, 293 cells, or NSO cells.

The production of the antibody or analog is then undertaken by culturing the modified recombinant host under culture conditions appropriate for the growth of the host cells and the expression of the coding sequences. The antibodies are then recovered from the culture. The expression systems are preferably designed to include signal peptides so that the resulting antibodies are secreted into the medium; however, intracellular production is also possible.

In addition to deliberate design of modified forms of the immunoglobulin genes to produce analogs, advantage can be taken of phage display techniques to provide libraries containing a repertoire of antibodies with varying affinities for the desired antigen. For production of such repertoires, it is unnecessary to immortalize the B cells from the immunized animal; rather, the primary B cells can be used directly as a source of DNA. The mixture of cDNAs obtained from B cells, e.g., derived from spleens, is used to prepare an expression library, for example, a phage display library transfected into E. coli. The resulting cells are tested for immunoreactivity to the desired antigen. Techniques for the identification of high affinity human antibodies from such libraries are described by Griffiths, A. D., et al., EMBO J (1994) 13:3245–3260; by Nissim, A., et al. ibid, 692–698, and by Griffiths, A. D., et al., ibid, 12:725–734. Ultimately, clones from the library are identified which produce binding affinities of a desired magnitude for the antigen, and the DNA encoding the product responsible for such binding is recovered and manipulated for standard recombinant expression. Phage display libraries may also be constructed using previously manipulated nucleotide sequences and screened in similar fashion. In general, the cDNAs encoding heavy and light chain are independently supplied or are linked to form $F_v$ analogs for production in the phage library.

The phage library is then screened for the antibodies with highest affinity for the antigen and the genetic material recovered from the appropriate clone. Further rounds of screening can increase the affinity of the original antibody isolated. The manipulations described above for recombinant production of the antibody or modification to form a desired analog can then be employed.

Combination of phage display technology with the XenoMouse™ offers a significant advantage over previous applications of phage display. Typically, to generate a highly human antibody by phage display, a combinatorial antibody library is prepared either from human bone marrow or from peripheral blood lymphocytes as described by Burton, D. R., et al., Proc. Natl. Acad. Sci. USA (1991) 88:10134–10137. Using this approach, it has been possible to isolate high affinity antibodies to human pathogens from infected individuals, i.e. from individuals who have been "immunized" as described in Burton, D. R., et al., Proc. Natl. Acad. Sci. USA (1991) 88:10134–10137, Zebedee, S. L., et al. Proc. Natl. Acad. Sci. USA (1992) 89:3175–3179, and Barbas III, C. F., et al., Proc. Natl. Acad. Sci. USA (1991) 89:10164–20168. However, to generate antibodies reactive with human antigens, it has been necessary to generate synthetic libraries (Barbas III C. F., et al., Proc. Natl. Acad. Sci. USA (1991) 89:4457–4461, Crameri, A. et al., BioTechnicues (1995) 88:194–196) or to prepare libraries from either autoimmune patients (Rapoport, B., et al., Immunol. Today (1995) 16:43–49, Portolano, S., et al., J. Immunol. (1993) 151:2839–2851, and Vogel, M., et al., Eur J. Immunol. (1994) 24:1200–1207) or normal individuals, i.e. naive libraries (Griffiths, A. D., et al., EMBO J. (1994) 13:3245–3260, Griffiths, A. D., et al., EMBO J. (1993) 12:725–734, Persson, M. A. A., et al., Proc. Natl. Acad. Sci. USA (1991) 88:2432–2436, Griffiths, A. D., Curr. Opin. Immunol. (1993) 5:263–267, Hoogenboom, H. R., et al., J. Mol. Biol. (1992) 227:381–388, Lerner, R. A., et al., Science (1992) 258:1313–1314, and Nissim A., et al., EMBO J. (1994) 13:692–698. Typically, high affinity antibodies to human proteins have proven very difficult to isolate in this way. As is well known, affinity maturation requires somatic mutation and somatic mutation, in turn, is antigen driven. In the XenoMouse, repeated immunization with human proteins will lead to somatic mutation and, consequently, high affinity antibodies. The genes encoding these antibodies can be readily amplified by PCR as described in Marks, J. D., et al., *J. Mol. Biol.* (1991) 581–596 and immunospecific antibodies isolated by standard panning techniques, Winter, G., et al.,*Annu. Rev. Immunol.* (1994) 12:433–55 and Barbas III, C. F., et al., *Proc. Natl. Acad. Sci. USA* (1991) 88:7978–7982.

As above, the modified or unmodified rearranged loci are manipulated using standard recombinant techniques by constructing expression systems operable in a desired host cell, such as, typically, a Chinese hamster ovary cell, and the desired immunoglobulin or analog is produced using standard recombinant expression techniques, and recovered and purified using conventional methods.

The application of the foregoing processes to antibody production has enabled the preparation of human immunospecific reagents with respect to antigens for which human antibodies have not heretofore been available. The immunoglobulins that result from the above-described methods and the analogs made possible thereby provide novel compositions for use in analysis, diagnosis, research, and therapy. The particular use will, of course, depend on the immunoglobulin or analog prepared. In general, the compositions of the invention will have utilities similar to those ascribable to nonhuman antibodies directed against the same antigen. Such utilities include, for example, use as affinity ligands for purification, as reagents in immunoassays, as components of immunoconjugates, and as therapeutic agents for appropriate indications.

Particularly in the case of therapeutic agents or diagnostic agents for use in vivo, it is highly advantageous to employ antibodies or their analogs with fully human characteristics. These reagents avoid the undesired immune responses engendered by antibodies or analogs which have characteristics marking them as originating from nonhuman species. Other attempts to "humanize" antibodies do not result in reagents with fully human characteristics. For example, chimeric antibodies with murine variable regions and human constant regions are easily prepared, but, of course, retain murine characteristics in the variable regions. Even the much more difficult procedure of "humanizing" the variable regions by manipulating the genes encoding the amino acid sequences that form the framework regions does not provide the desired result since the CDRs, typically of nonhuman origin, cannot be manipulated without destroying immunospecificity.

Thus, the methods of the present invention provide, for the first time, immunoglobulins that are fully human or analogs which contain immunospecific regions with fully human characteristics.

There are large numbers of antigens for which human antibodies and their human analogs would be made available by the methods of the invention. These include, but are not limited to, the following nonlimiting set:

leukocyte markers, such as CD2, CD3, CD4, CD5, CD6, CD7, CD8, CD11a,b,c, CD13, CD14, CD18, CD19, CD20, CD22, CD23, CD27 and its ligand, CD28 and its ligands B7.1, B7.2, B7.3, CD29 and its ligand, CD30 and its ligand, CD40 and its ligand gp39, CD44, CD45 and isoforms, Cdw52 (Campath antigen), CD56, CD58, CD69, CD72, CTLA-4, LFA-1 and TCR histocompatibility antigens, such as MHC class I or II, the Lewis Y antigens, Slex, Sley, Slea, and Selb;

adhesion molecules, including the integrins, such as VLA-1, VLA-2, VLA-3, VLA-4, VLA-5, VLA-6, LFA-1, Mac-1, $\alpha V\beta 3$, and p150,95; and the selectins, such as L-selectin, E-selectin, and P-selectin and their counterreceptors VCAM-1, ICAM-1, ICAM-2, and LFA-3;

interleukins, such as IL-1, IL-2, IL-3, IL-4, IL-5, IL-6, IL-7, IL-8, IL-9, IL-10, IL-11, IL-12, IL-13, IL-14, and IL-15;

interleukin receptors, such as IL-1R, IL-2R, IL-3R, IL-4R, IL-5R, IL-6R, IL-7R, IL-8R, IL-9R, IL-10R, IL-11R, IL-12R, IL-13R, IL-14R and IL-15R;

chemokines, such as PF4, RANTES, MIPla, MCP1, IP-10, ENA-78, NAP-2, Gro$\alpha$, Gro$\beta$, and IL-8;

growth factors, such as TNFalpha, TGFbeta, TSH, VEGF/VPF, PTHrP, EGF family, FGF, PDGF family, endothelin, Fibrosin ($F_S F_{-1}$), Laminin, and gastrin releasing peptide (GRP);

growth factor receptors, such as TNFalphaR, RGFbetaR, TSHR, VEGFR/VPFR, FGFR, EGFR, PTHrPR, PDGFR family, EPO-R, GCSF-R and other hematopoietic receptors;

interferon receptors, such as IFN$\alpha$R, IFN$\beta$R, and IFN$_\gamma$R;

Igs and their receptors, such as IGE, FceRI, and FceRII;

tumor antigens, such as her2-neu, mucin, CEA and endosialin;

allergens, such as house dust mite antigen, lol p1 (grass) antigens, and urushiol;

viral proteins, such as CMV glycoproteins B, H, and gCIII, HIV-1 envelope glycoproteins, RSV envelope glycoproteins, HSV envelope glycoproteins, EBV envelope glycoproteins, VZV, envelope glycoproteins, HPV envelope glycoproteins, Hepatitis family surface antigens;

toxins, such as pseudomonas endotoxin and osteopontin/uropontin, snake venom, spider venom, and bee venom;

blood factors, such as complement C3b, complement C5a, complement C5b-9, Rh factor, fibrinogen, fibrin, and myelin associated growth inhibitor;

enzymes, such as cholesterol ester transfer protein, membrane bound matrix metalloproteases, and glutamic acid decarboxylase (GAD); and miscellaneous antigens including ganglioside GD3, ganglioside GM2, LMP1, LMP2, eosinophil major basic protein, PTHrp, eosinophil cationic protein, pANCA, Amadori protein, Type IV collagen, glycated lipids, v-interferon, A7, P-glycoprotein and Fas (AFO-1) and oxidized-LDL.

Particularly preferred immunoglobulins and analogs are those immunospecific with respect to human IL-6, human IL-8, human TNF$\alpha$, human CD4, human L-selectin, human PTHrp and human gp39. Antibodies and analogs immunoreactive with human TNF$\alpha$ and human IL-6 are useful in treating cachexia and septic shock as well as autoimmune disease. Antibodies and analogs immunoreactive with GP39 or with L-selectin are also effective in treating or preventing autoimmune disease. In addition, anti-gp39 is helpful in treating graft versus host disease, in preventing organ transplant rejection, and in treating glomerulonephritis. Antibodies and analogs against L-selectin are useful in treating ischemia associated with reperfusion injury. Antibodies to PTHrp are useful in treating bone disease and metastatic cancer. In a particular embodiment, human antibodies against IL-8 may be used for the treatment or prevention of a pathology or condition associated with IL-8. Such conditions include, but are not limited to, tumor metastasis, reperfusion injury, pulmonary edema, asthma, ischemic disease such as myocardial infarction, inflammatory bowel disease (such as Crohn's disease and ulcerative colitis), encephalitis, uveitis, autoimmune diseases (such as rheumatoid arthritis, Sjögren's syndrome, vasculitis), osteoarthritis, gouty arthritis, nephritis, renal failure, dermatological conditions such as inflammatory dermatitis, psoriasis, vasculitic urticaria and allergic angiitis, retinal uveitis, conjunctivitis, neurological disorders such as stroke, multiple sclerosis and meningitis, acute lung injury, adult respiratory distress syndrome (ARDS), septic shock, bacterial pneumonia, diseases involving leukocyte diapedesis, CNS inflammatory disorder, multiple organ failure, alcoholic hepatitis, antigen-antibody complex mediated diseases, inflammation of the lung (such as pleurisy, aveolitis, vasculitis, pneumonia, chronic bronchitis, bronchiectasis, cystic fibrosis), Behcet disease, Wegener's granulomatosis, and vasculitic syndrome.

Typical autoimmune diseases which can be treated using the above-mentioned antibodies and analogs include systemic lupus erythematosus, rheumatoid arthritis, psoriasis, Sjogren's scleroderma, mixed connective tissue disease, dermatomyositis, polymyositis, Reiter's syndrome, Behcet's disease, Type 1 diabetes, Hashimoto's thyroiditis, Grave's disease, multiple sclerosis, myasthenia gravis and pemphigus.

For therapeutic applications, the antibodies may be administered in a pharmaceutically acceptable dosage form. They may be administered by any means that enables the active agent to reach the desired site of action, for example, intravenously as by bolus or by continuous infusion over a period of time, by intramuscular, subcutaneous, intraarticular, intrasynovial, intrathecal, oral, topical or inhalation routes. The antibodies may be administered as a single dose or a series of treatments.

For parenteral administration, the antibodies may be formulated as a solution, suspension, emulsion or lyophilized powder in association with a pharmaceutically acceptable parenteral vehicle. If the antibody is suitable for oral administration, the formulation may contain suitable additives such as, for example, starch, cellulose, silica, various sugars, magnesium carbonate, or calcium phosphate. Suitable vehicles are described in the most recent edition of Remington's Pharmaceutical Sciences, A. Osol, a standard reference text in this field.

For prevention or treatment of disease, the appropriate dosage of antibody will depend upon known factors such as the pharmacodynamic characteristics of the particular antibody, its mode and route of administration, the age, weight, and health of the recipient, the type of condition to be treated and the severity and course of the condition, frequency of treatment, concurrent treatment and the physiological effect desired. The examples below are intended to illustrate but not to limit the invention.

In these examples, mice, designated XenoMouse™, are used for initial immunizations. A detailed description of the XenoMouse™ is found in the above referenced PCT application WO 94/02602. Immunization protocols appropriate to each antigen are described in the specific examples below. The sera of the immunized XenoMouse™ (or the supernatants from immortalized B cells) were titrated for antigen specific human antibodies in each case using a standard ELISA format. In this format, the antigen used for immunization was immobilized onto wells of microtiter plates. The plates were washed and blocked and the sera (or supernatants) were added as serial dilutions for 1–2 hours of incubation. After washing, bound antibody having human characteristics was detected by adding antihuman κ, $\mu$, or $\gamma$ chain antibody conjugated to horseradish peroxidase (HRP) for one hour. After again washing, the chromogenic reagent o-phenylene diamine (OPD) substrate and hydrogen peroxide were added and the plates were read 30 minutes later at 492 nm using a microplate reader.

Unless otherwise noted, the antigen was coated using plate coating buffer (0.1 M carbonate buffer, pH 9.6); the assay blocking buffer used was 0.5% BSA, 0.1% Tween 20 and 0.01% thimerosal in PBS; the substrate buffer used in color development was citric acid 7.14 g/l; dibasic sodium phosphate 17.96 g/l; the developing solution (made immediately before use) was 10 ml substrate buffer; 10 mg OPD, plus 5 ml hydrogen peroxide; the stop solution (used to stop color development) was 2 M sulfuric acid. The wash solution was 0.05% Tween 20 in PBS.

EXAMPLE 1

Human Antibodies Against Human IL-6

Three to five XenoMouse™ aged 8–20 weeks were age-matched and immunized intraperitoneally with 50 $\mu$g human IL-6 emulsified in incomplete Freund's adjuvant for primary immunization and in complete Freund's adjuvant for subsequent injections. The mice received 6 injections 2–3 weeks apart. Serum titers were determined after the second dose and following each dose thereafter. Bleeds were performed from the retrobulbar plexus 6–7 days after injections. The blood was allowed to clot at room temperature for about 2 hours and then incubated at 4° C. for at least 2 hours before separating and collecting the sera.

ELISAs were conducted as described above by applying 100 $\mu$l/well of recombinant human IL-6 at 2 $\mu$g/ml in coating buffer. Plates were then incubated at 4° C. overnight or at 37° C. for 2 hours and then washed three times in washing buffer. Addition of 100 $\mu$l/well blocking buffer was followed by incubation at room temperature for 2 hours, and an additional 3 washes.

Then, 50 $\mu$l/well of diluted serum samples (and positive and negative controls) were added to the plates. Plates were then incubated at room temperature for 2 hours and again washed 3 times.

Figure 3:
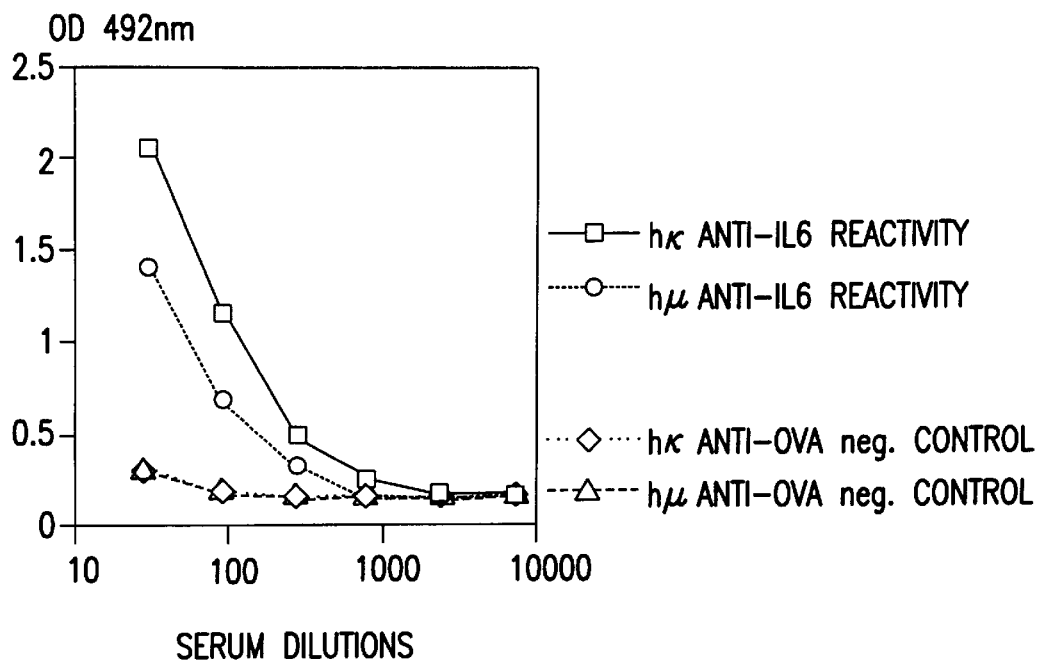
FIG. 3 shows the serum titers of anti-IL-6 antibodies from a XenoMouse™ immunized with human IL-6 and which antibodies contain human κ light chains and/or human μ heavy chains.

After washing, 100 $\mu$l/well of either mouse antihuman $\mu$ chain antibody conjugated to HRP at $\frac{1}{2,000}$ or mouse antihuman κ chain antibody conjugated to HRP at $\frac{1}{2,000}$, diluted in blocking buffer was added. After a 1 hour incubation at room temperature, the plates were washed 3 times and developed with OPD substrate for 10–25 minutes. 50 $\mu$l/well of stop solution was then added and the results read on an ELISA plate reader at 492 nm. The dilution curves resulting from the titration of serum from XenoMouse™ after 6 injections are shown in FIG. 3. The data in FIG. 3 show production of anti-IL-6 immunoreactive with antihuman κ and antihuman $\mu$ detectable at serum dilutions above 1:1,000.

EXAMPLE 2

Human Antibodies Against Human TNFα

Immunization and serum preparation were conducted as described in Example 1 except that human recombinant TNFα (at 5 $\mu$g per injection) was substituted for human IL-6. ELISAs were conducted as described in Example 1 except that the initial coating of the ELISA plate employed 100 $\mu$l/well recombinant human TNFA at 1 $\mu$g/ml in coating buffer.

Figure 4:
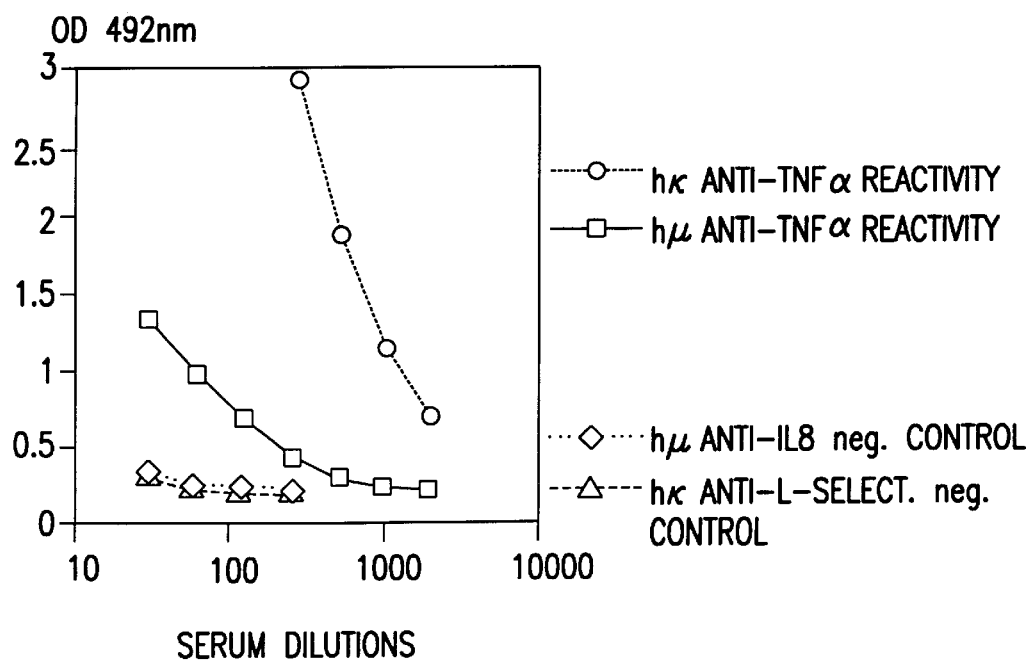
FIG. 4 show the serum titers of anti-TNFα antibodies from a XenoMouse™ immunized with human TNF-α and which antibodies contain human κ light chains and/or human μ heavy chains.

The dilution curves for serum from XenoMouse™ after 6 injections obtained are shown in FIG. 4. Again significant titers of human anti-TNFα binding were shown.

Serum titers for hγ, h$\mu$, and hκ after one and two immunizations of the XenoMouse™ are shown in Table 1. When challenged with TNF-α, the XenoMouse™ switches isotypes from a predominant IgM response in the first immunization to an immune response with a large IgG component in the second immunization.

TABLE 1

Anti TNF-alpha serum titer responses of Xenomouse-2.

| XM2 | | ELISA Serum titers Specific for TNF-alpha | | |
|---|---|---|---|---|
| | | titer (via hγ) | titer (via hμ) | titer (via hκ) |
| 1 | bleed 1 | 500 | 3,000 | 1,500 |
|   | bleed 2 | 10,000 | 8,000 | 15,000 |
| 2 | bleed 1 | 200 | 3,000 | 500 |
|   | bleed 2 | 2,700 | 5,000 | 1,000 |
| 3 | bleed 1 | <500 | 2,000 | 1,500 |
|   | bleed 2 | 15,000 | 24,000 | 25,000 |
| 4 | bleed 1 | 500 | 2,500 | 1,500 |
|   | bleed 2 | 70,000 | 4,000 | 72,000 |
| 5 | bleed 1 | <500 | 2,500 | 1,500 |
|   | bleed 2 | 1,000 | 10,000 | 7,000 |
| 6 | bleed 1 | 1,000 | 13,000 | 4,500 |
|   | bleed 2 | 10,000 | 24,000 | 25,000 |
| 7 | bleed 1 | <500 | 2,500 | 1,500 |
|   | bleed 2 | 5,000 | 4,000 | 9,000 |
| 8 | bleed 1 | <500 | 1,000 | 500 |
|   | bleed 2 | 2,700 | 5,000 | 9,000 |
| 9 | bleed 1 | 200 | 6,000 | 4,000 |
|   | bleed 2 | 40,000 | 80,000 | 80,000 |
| 10 | bleed 1 | 200 | 2,000 | 500 |
|    | bleed 2 | 15,000 | 8,000 | 60,000 |
| 11 | bleed 1 | 1,500 | 1,000 | 1,500 |
|    | bleed 2 | 24,000 | 2,700 | 72,000 |
| 12 | bleed 1 | 200 | 2,000 | 1,000 |
|    | bleed 2 | 10,000 | 4,000 | 25,000 |
| 13 | bleed 1 | 500 | 30,000 | 500 |
|    | bleed 2 | 2,000 | 4,000 | 12,000 |

Bleed 1: after 2 immunizations
Bleed 2: after 3 immunizations

EXAMPLE 3

Human antibodies Against Human CD4

The human CD4 antigen was prepared as a surface protein using human CD4ζ on transfected recombinant cells as follows. Human CD4ζ consists of the extracellular domain of CD4, the transmembrane domain of CD4, and the cytoplasmic domain corresponding to residues 31–142, of the mature ζ chain of the CD3 complex. Human CD4 zeta (F15 LTR) as described in Roberts et al., *Blood* (1994) 84:2878 was introduced into the rat basophil leukemic cell line RBL-2H3, described by Callan, M., et al., *Proc Natl Acad Sci USA* (1993) 90:10454 using the Kat high efficiency transduction described by Finer et al., *Blood* (1994) 83:43. Briefly, RBL-2H3 cells at $10^6$ cells per well were cultured in 750 μl DMEM$^{low}$ +20% FBS (Gibco) and 16 μg/ml polybrene with an equal volume of proviral supernatant for 2 hours at 37° C., 5% $CO_2$. One ml of medium was removed and 750 μl of infection medium and retroviral supernatant were added to each well and the cultures incubated overnight. The cells were washed and expanded in DMEM$^{low}$+ 10% FBS until sufficient cells were available for sorting. The CD4 zeta transduced RBL-2H3 cells were sorted using the FACSTAR plus (Becton Dickinson). The cells were stained for human CD4 with a mouse antihuman CD4 PE antibody and the top 2–3% expressing cells were selected.

Figure 5:
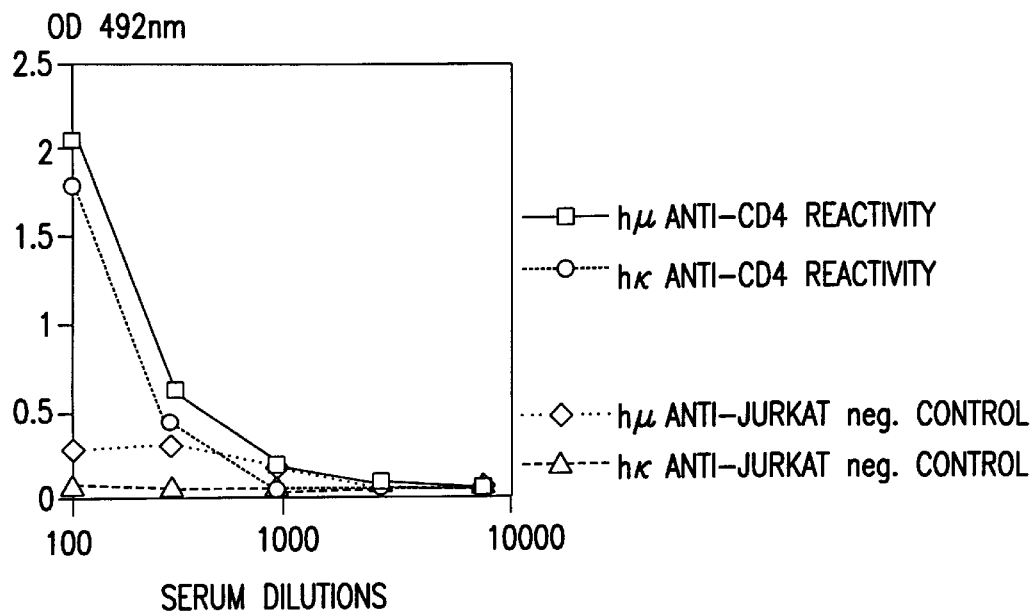
FIG. 5 shows serum titers of anti-CD4 antibodies from a XenoMouse™ immunized with human CD4 and which antibodies contain human κ light chains and/or human μ heavy chains.

Immunizations were conducted as described in Example 1 using $1 \times 10^7$ cells per mouse except that the primary injection was subcutaneous at the base of the neck. The mice received 6 injections 2–3 weeks apart. Serum was prepared and analyzed by ELISA as described in Example 1 except that the initial coating of the ELISA plate utilized 100 μl per well of recombinant soluble CD4 at 2 μg/ml of coating buffer. The titration curve for serum from XenoMouse™ after 6 injections is shown in FIG. 5. Titers of human anti-CD4 reactivity were shown at concentrations representing greater than those of 1:1,000 dilution.

EXAMPLE 4

Human Antibodies Against Human L-selectin

The antigen was prepared as a surface displayed protein in C51 cells, a high expressing clone derived by transfecting the mouse pre-B cell 300.19 with LAM-1 cDNA (LAM-1 is the gene encoding L-selectin) (Tedder, et al., *J. Immunol* (1990) 144:532) or with similarly transfected CHO cells. The transfected cells were sorted using fluorescent activated cell sorting using anti-Leu-8 antibody as label.

The C51 and the transfected CHO cells were grown in DME 4.5 g/I glucose with 10% FCS and 1 mg/ml G418 in 100 mm dishes. Negative control cells, 3T3-P317 (transfected with gag/pol/env genes of Moloney virus) were grown in the same medium without G418.

Primary immunization was done by injection subcutaneously at the base of the neck; subsequent injections were intraperitoneal. 70–100 million C51 or transfected CHO cells were used per injection for a total of five injections 2–3 weeks apart.

Sera were collected as described in Example 1 and analyzed by ELISA in a protocol similar to that set forth in Example 1.

For the ELISA, the transfected cells were plated into 96 well plates and cell monolayers grown for 1–2 days depending on cell number and used for ELISA when confluent. The cells were fixed by first washing with cold 1 x PBS and then fixing solution (5% glacial acetic acid, 95% ethanol) was added. The plates were incubated at −25° C. for 5 minutes and can be stored at this temperature if sealed with plate sealers.

The ELISA is begun by bringing the plates to room temperature, flicking to remove fixing solution and washing 5 times with DMEM medium containing 10% FCS at 200 μl per well.

The wells were treated with various serum dilutions or with positive or negative controls. Positive control wells contained murine IgG1 monoclonal antibody to human L-selectin.

Figure 6:
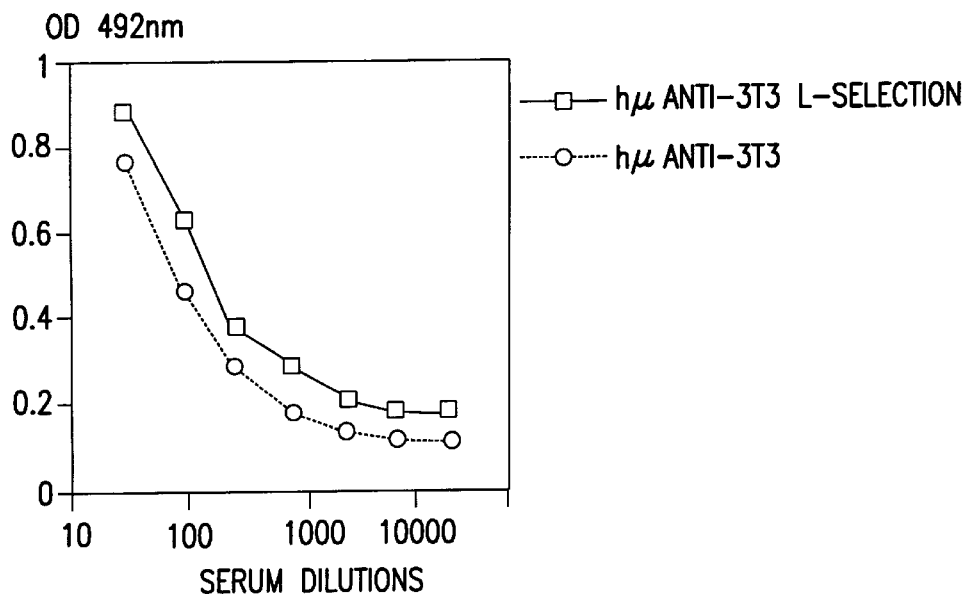
FIG. 6 shows the serum titers of a XenoMouse™ immunized with 300.19 cells expressing L-selectin at their surface. In the ELISA assay used, these antibodies are detectable if they carry human μ constant region heavy chains.
Figure 7:
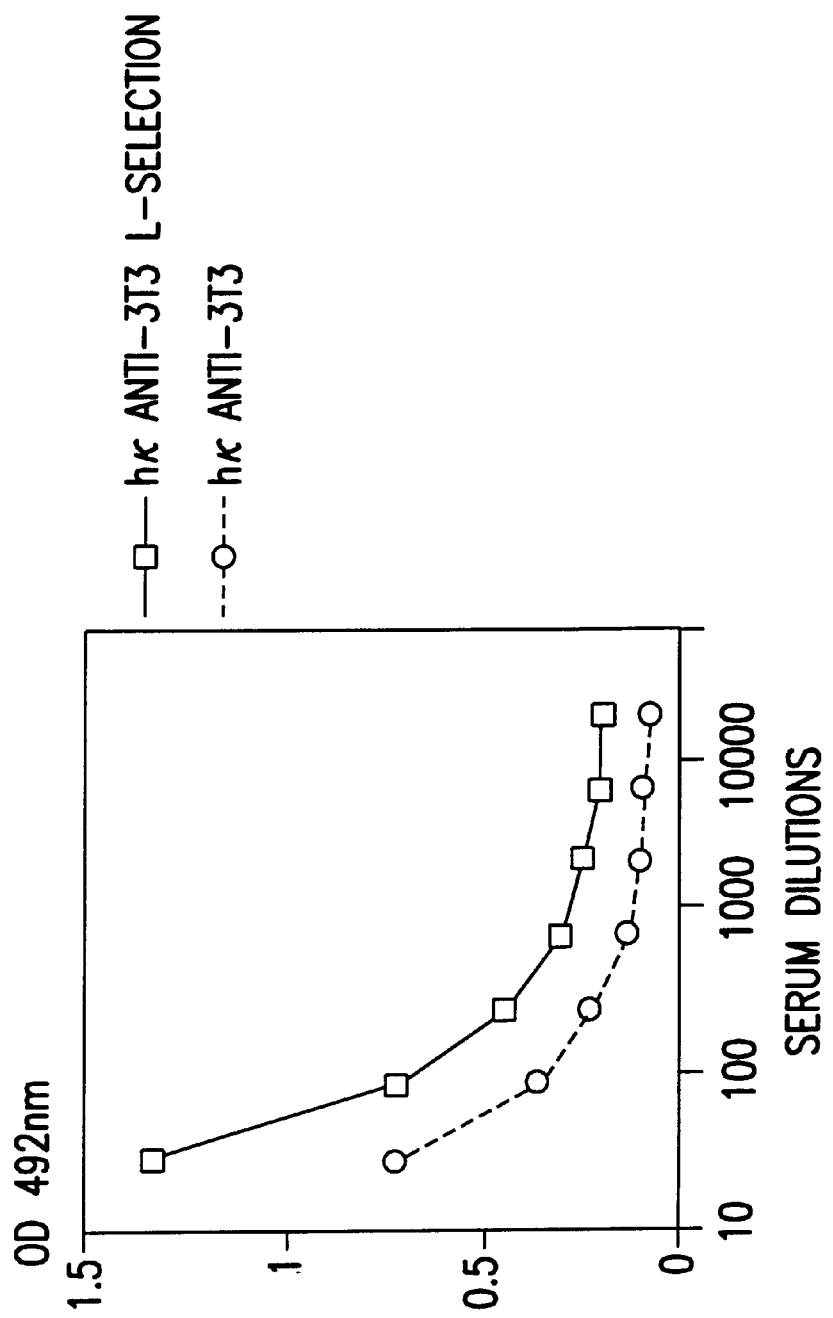
FIG. 7 shows the serum titers of a XenoMouse™ immunized with 300.19 cells expressing L-selectin at their surface. In the ELISA assay used, these antibodies are detectable only if they carry human κ light chains.

The wells were incubated for 45 minutes and monolayer integrity was checked under a microscope. The wells were then incubated with antihuman κ chain antibody or antihuman μ chain antibody conjugates with HRP described in Example 1. The plates were then washed with 1% BSA/PBS and again with PBS and monolayer integrity was checked. The plates were developed, stopped, and read as described above. The results for serum from XenoMouse™ are shown in FIGS. 6 and 7; human antibodies both to L-selectin and control 3T3 cells were obtained. However, the serum titers are higher for the L-selectin-expressing cells as compared to parental 3T3 cells. These results show the XenoMouse™ produces antibodies specific for L-selectin with human μ heavy chain regions and human κ light chains.

The antisera obtained from the immunized XenoMouse™ were also tested for staining of human neutrophils which express L-selectin. Human neutrophils were prepared as follows: peripheral blood was collected from normal volunteers with 100 units/ml heparin. About 3.5 ml blood was layered over an equal volume of One-step Polymorph Gradient (Accurate Chemical, Westbury, N.Y.) and spun for 30 minutes at 450 x g at 20° C. The neutrophil fraction was removed and washed twice in DPBS/2% FBS.

The neutrophils were then stained with either;

(1) antiserum from XenoMouse™ immunized with C51 cells (expressing L-selectin);

(2) as a negative control, antiserum from a XenoMouse™ immunized with cells expressing human gp39.

Figure 8:
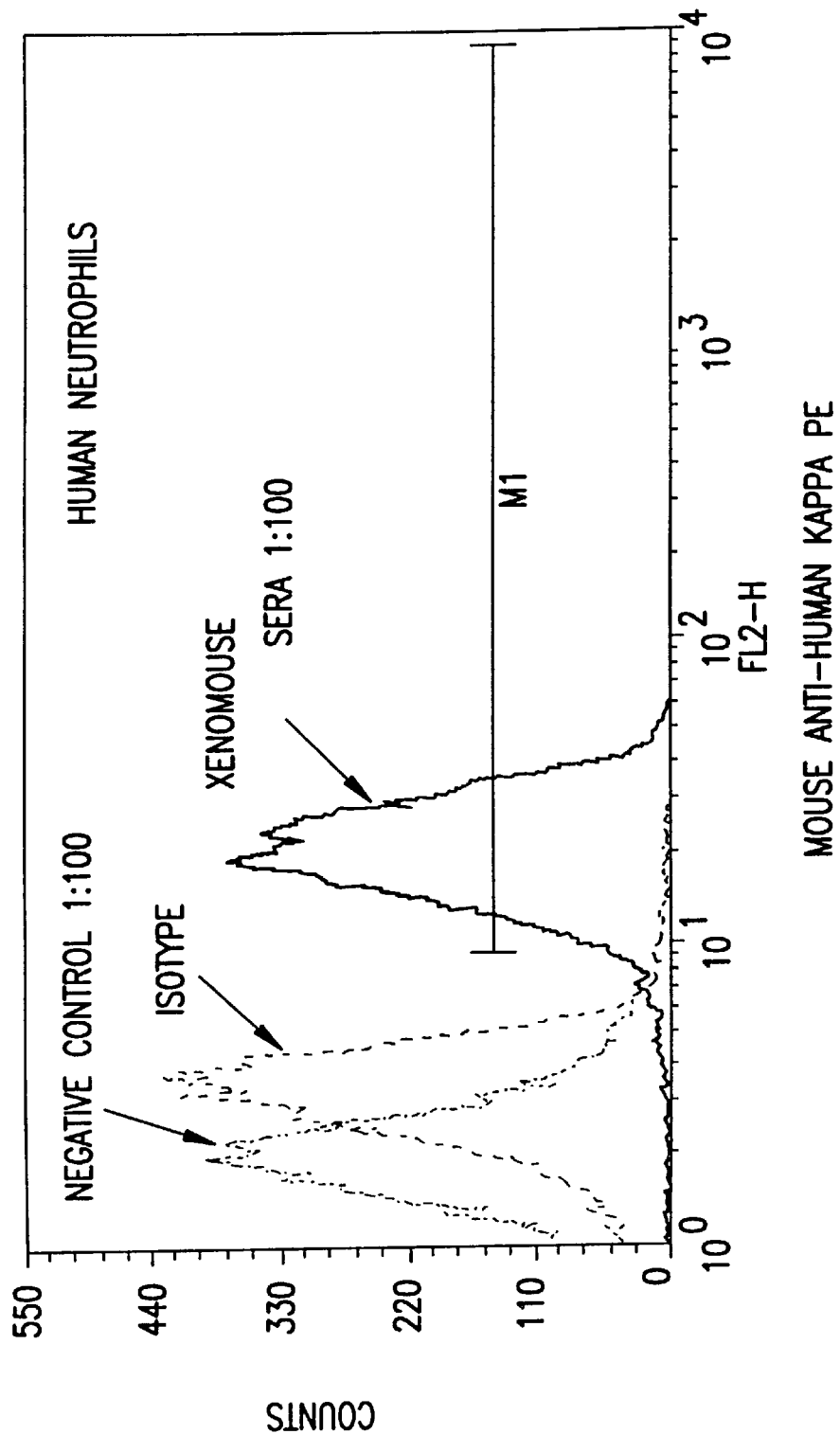
FIG. 8 shows a FACS Analysis of human neutrophils incubated with serum from a XenoMouse™ immunized with human L-selectin and labeled with an antibody immunoreactive with human light chain κ region.

The stained, washed neutrophils were analyzed by FACS. The results for antiserum from XenoMouse™ are shown in FIG. 8.

These results show the presence of antibodies in immunized XenoMouse™ serum which contain fully human light chains immunoreactive with L-selectin. The negative control antiserum from mice immunized with gp39 does not contain antibodies reactive against human neutrophils.

EXAMPLE 5

Human Antibodies Against Human gp39 gp39 (the ligand for CD40) is expressed on activated human CD4 T cells. The sera of XenoMouse™ immunized with recombinant gp39 according to this example contained fully human antibodies immunospecific for gp39.

Figure 9:
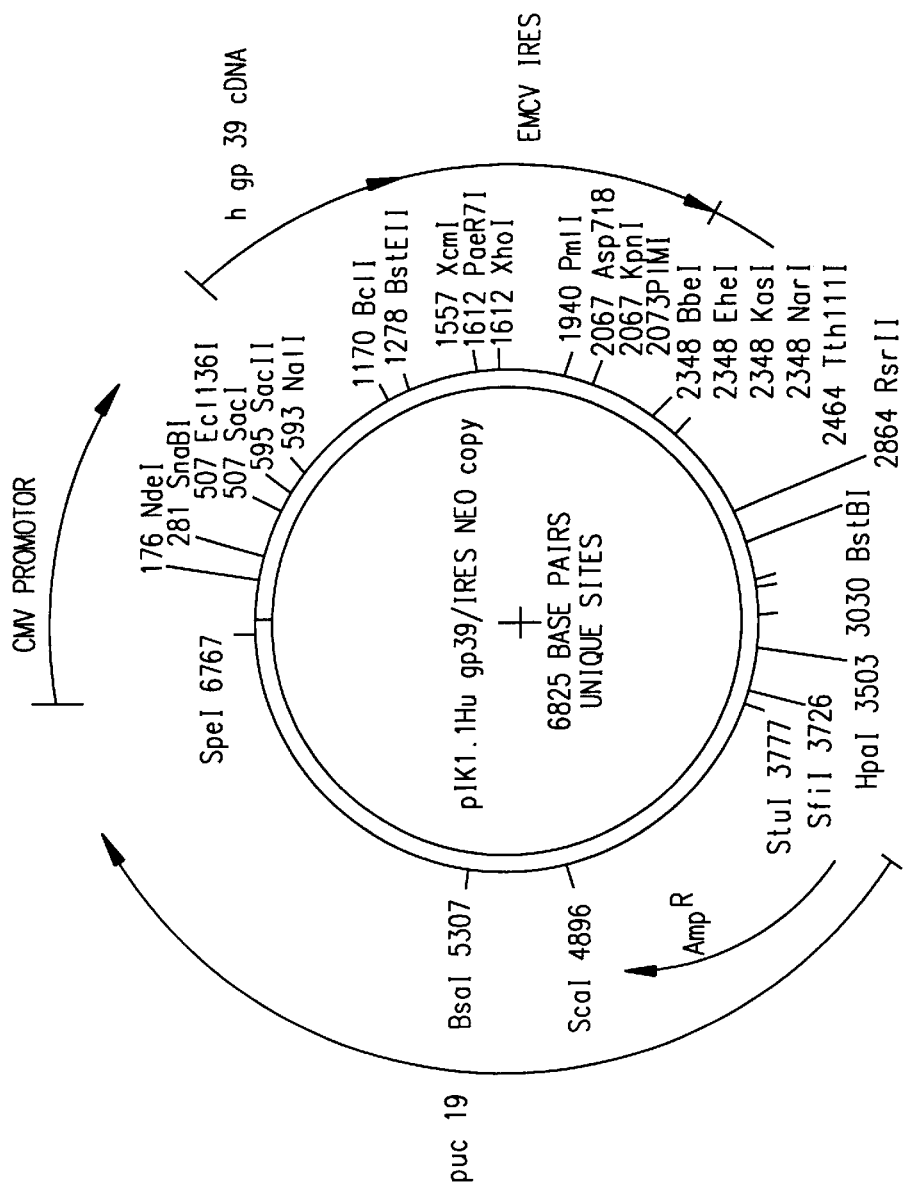
FIG. 9 shows a diagram of a plasmid used to transfect mammalian cells to effect the production of the human protein gp39.

The antigen consisted of stable transfectants of 300.19 cells or of CHO cells expressing gp39 cDNA cloned into the mammalian expression vector P1K1.HUgp39/IRES NEO as shown in FIG. 9. CHO cells were split 1:10 prior to transfection in DMEM 4.5 g/l glucose, 10% FBS, 2 mM glutamine, MEM, NEAA supplemented with additional glycine, hypoxanthine and thymidine. The cells were cotransfected with the gp39 vector at 9 μg/10 cm plate ($6 \times 10^5$ cells) and the DHFR expressing vector pSV2DHFRs (Subranani et al., *Mol Cell Biol* (1981) 9:854) at 1 μg/10 cm plate using calcium phosphate transfection. 24 hours later the cells were split 1:10 into the original medium containing G418 at 0.6 mg/ml. Cells producing gp39 were sorted by FACS using an anti-gp39 antibody.

Mice grouped as described in Example 1 were immunized with 300.19 cells expressing gp39 using primary immunization subcutaneously at the base of the neck and with secondary intraperitoneal injections every 2–3 weeks. Sera were harvested as described in Example 1 for the ELISA assay. The ELISA procedure was conducted substantially as set forth in Example 1; the microtiter plates were coated with CHO cells expressing gp39 grown in a 100 mm dish in DMEM, 4.5 g/l glucose, 10% FCS, 4mM glutamine, and nonessential amino acid (NEAA) solution for MEM (100X). On the day preceding the ELISA assay, the cells were trypsinized and plated into well filtration plates at $10^5$ cells/200 μl well and incubated at 37° C. overnight. The positive controls were mouse antihuman gp39; negative controls were antisera from mice immunized with an antigen other than gp39. 50 μl of sample were used for each assay. The remainder of the assay is as described in Example 1.

Figure 10:
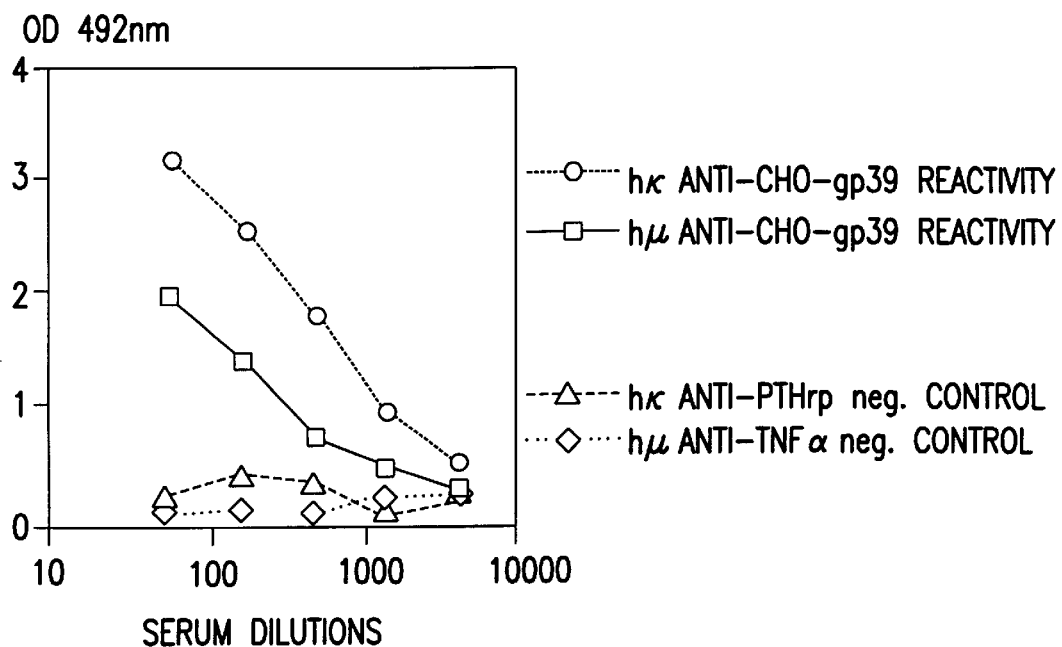
FIG. 10 represents the serum titration curve of mice immunized with CHO cells expressing human gp39. The antibodies detected in this ELISA must be immunoreactive with gp39 and contain human heavy chain μ constant regions of human κ light chains.

The dilution curves for the sera obtained after 4 injections from mice immunized with gp39 expressed on CHO cells are shown in FIG. 10. As shown, the sera contained anti-human gp39 immunospecificity which is detectable with anti-human κ and anti-human μ chain antibodies coupled to HRP.

EXAMPLE 6

Preparation of Human Mabs Against Tetanus Toxin

The antibodies prepared in this example were secreted by hybridomas obtained by immortalizing B cells from xenomice immunized with tetanus toxin. The immunization protocol was similar to that set forth in Example 1 using 50 μg tetanus toxin emulsified in complete Freund's adjuvant for intraperitoneal primary immunization followed by subsequent intraperitoneal injections with antigen incorporated into incomplete Freund's adjuvant. The mice received a total of 4 injections 2–3 weeks apart.

After acceptable serum titers of antitetanus toxin C (anti-TTC) were obtained, a final immunization dose of antigen in PBS was give 4 days before the animals were sacrificed and the spleens were harvested for fusion.

The spleen cells were fused with myeloma cells P3X63-Ag8.653 as described by Galfre, G. and Milstein, C. *Methods in Enzymolovy* (1981) 73:3–46.

After fusion the cells were resuspended in DMEM, 15% FCS, containing HAT supplemented with glutamine, pen/strep for culture at 37° C. and 10% $CO_2$. The cells were plated in microtiter plates and maintained in HAT-supplemented medium for two weeks before transfer to HAT-supplemented medium. Supernatants from wells containing hybridomas were collected for a primary screen using an ELISA.

The ELISA was conducted as described in Example 1 wherein the antigen coating consisted of 100 μl/well of tetanus toxin C (TTC) protein at 2 μg/ml in coating buffer, followed by incubation at 4° C. overnight or at 37° C. for two hours. In the primary ELISA, HRP-conjugated mouse antihuman IgM was used as described in Example 1. Two hybridomas that secreted anti-TTC according to the ELISA assay, clone D5.1 and clone K4.1 were used for further analysis.

Figure 11:
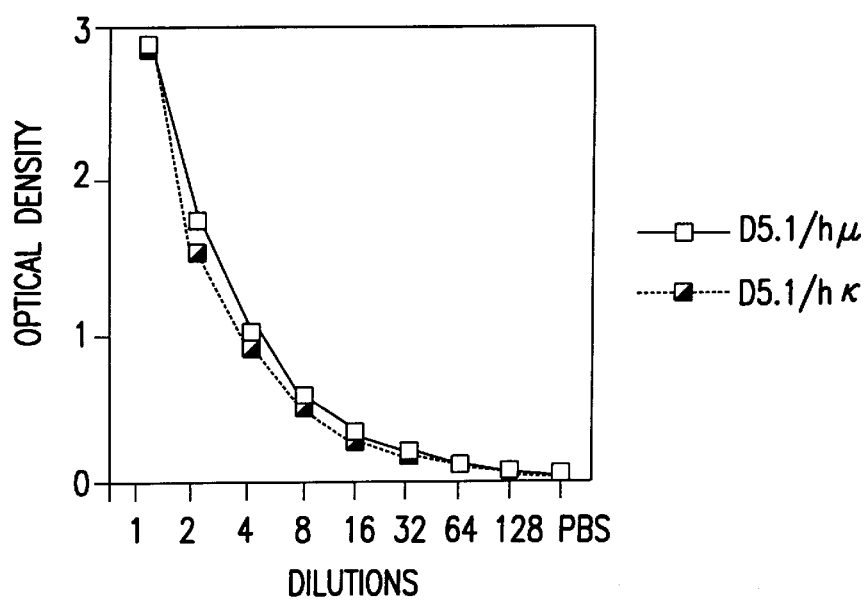
FIG. 11 is a titration curve with respect to monoclonal antibodies secreted by the hybridoma clone D5.1. This clone is obtained from a XenoMouse™ immunized with tetanus toxin C (TTC) and contains human γ light chain and human μ constant region in the heavy chain.

As shown in FIG. 11, clone D5.1 secretes fully human anti-TTC which is detectable using HRP-conjugated anti-human μ chain antibody and HRP-conjugated antihuman X chain antibody. This is confirmed in FIG. 11.

The antibody secreted by D5.1 did not immunoreact in ELISAs using TNFα, IL-6, or IL-8 as immobilized antigen under conditions where positive controls (sera from xenomice immunized with TNFα, IL-6 and IL-8 respectively) showed positive ELISA results.

The complete nucleotide sequence of the cDNAs encoding the heavy and light chains of the monoclonal were determined as shown in FIGS. 12 and 13. polyA mRNA was isolated from about $10^6$ hybridoma cells and used to generate cDNA using random hexamers as primers. Portions of the product were amplified by PCR using the appropriate primers.

The cell line was known to provide human κ0 light chains; for PCR amplification of light chain encoding cDNA, the primers used were HKP1 (5'-CTCTGTGACACTCTCCTGGGAGTT-3') (SEQ ID NO.18) for priming from the constant region terminus and two oligos, used in equal amounts to prime from the variable segments; B3 (5'-GAAACGACACTCACGCAGTCTCCAGC-3') (SEQ ID NO:19).

For amplification of the heavy chain of the antibody derived form D5.1 (which contains the human μ constant region), MG-24VI was used to prime from the variable and μP1 (5'-TTTTCTTTGTTGCCGTTGGGGTGC-3') (SEQ ID NO:20), was used to prime from the constant region terminus.

Referring to FIG. 12 which sets forth the sequence for the heavy chain of the antibody secreted by clone D5.1, this shows the heavy chain is comprised of the human variable fragment VH6, the human diversity region DN1 and the human joining segment JH4 linked to the human μ constant region. There were two base-pair mutations from the germline sequence in the variable region, both in the CDRs. Two additional mutations were in the D segment and six non-germline nucleotide additions were present at the $D_h$-$J_h$ junction.

Finally, referring to FIG. 13 which presents the light chain of the antibody secreted by D5.1, the human κ variable region B3 and human κ joining region JK3 are shown. There are nine base-pair differences from the germline sequences, three falling with CDR1.

EXAMPLE 7

Human Antibodies Against PTHrp

Groups of XenoMouse™-2 were immunized intraperitoneally with either PTHrp (1–34) conjugated with BTG, as described by Ratcliffe et al., *J. Immunol. Methods* 127:109 (1990), or with PTHrp (1–34) synthesized as a 4 branched-MAP (multiple antigenic peptide system). The antigens were emulsified in CFA (complete Freunds adjuvant) and injected i.p. at a dose of 25 μg per animal at 2 week intervals, and bled after two injections. The sera obtained from this bleed were analyzed by ELISA as described supra.

Serum titers for hγ, hμ, and hκ after one immunization of the XenoMouse™ are shown in Table 2. When immunized with PTHrp, the XenoMouse™ showed low serum titers in 5 of 7 mice on the first bleed, but when PTHrp-MAP is used, 7 of 7 mice show high serum titers on the first bleed.

TABLE 2

AntiPTHrp serum titer responses of Xenomouse-2.

| | Human Responses | | |
|---|---|---|---|
| | titer (via hγ) | titer (via hμ) | titer (via hκ) |
| XM2 PTHrp-BTG Conjugate | | | |
| 1 | <30 | 850 | 100 |
| 2 | <30 | 3,000 | 50 |
| 3 | <30 | 7,000 | 1,000 |
| 4 | <30 | 800 | 200 |
| 5 | <30 | 400 | 90 |
| 6 | <30 | 500 | 50 |
| 7 | <30 | 300 | 50 |
| XM2 PTHrp-MAP | | | |
| 1 | <30 | 1,000 | 50 |
| 2 | <30 | 2,500 | 300 |
| 3 | <30 | 1,200 | 150 |
| 4 | 150 | 1,000 | 270 |
| 5 | 100 | 2,500 | 300 |
| 6 | <30 | 1,000 | 150 |
| 7 | <30 | 4,000 | 800 |

First bleed after 2 immunizations with either PTHrp-BTG conjugate

EXAMPLE 8

Human Antibodies Against Human IL-8

Immunization and serum preparation were as described in Example 1 except that human recombinant IL-8 was used as an immunogen.

Figure 14:
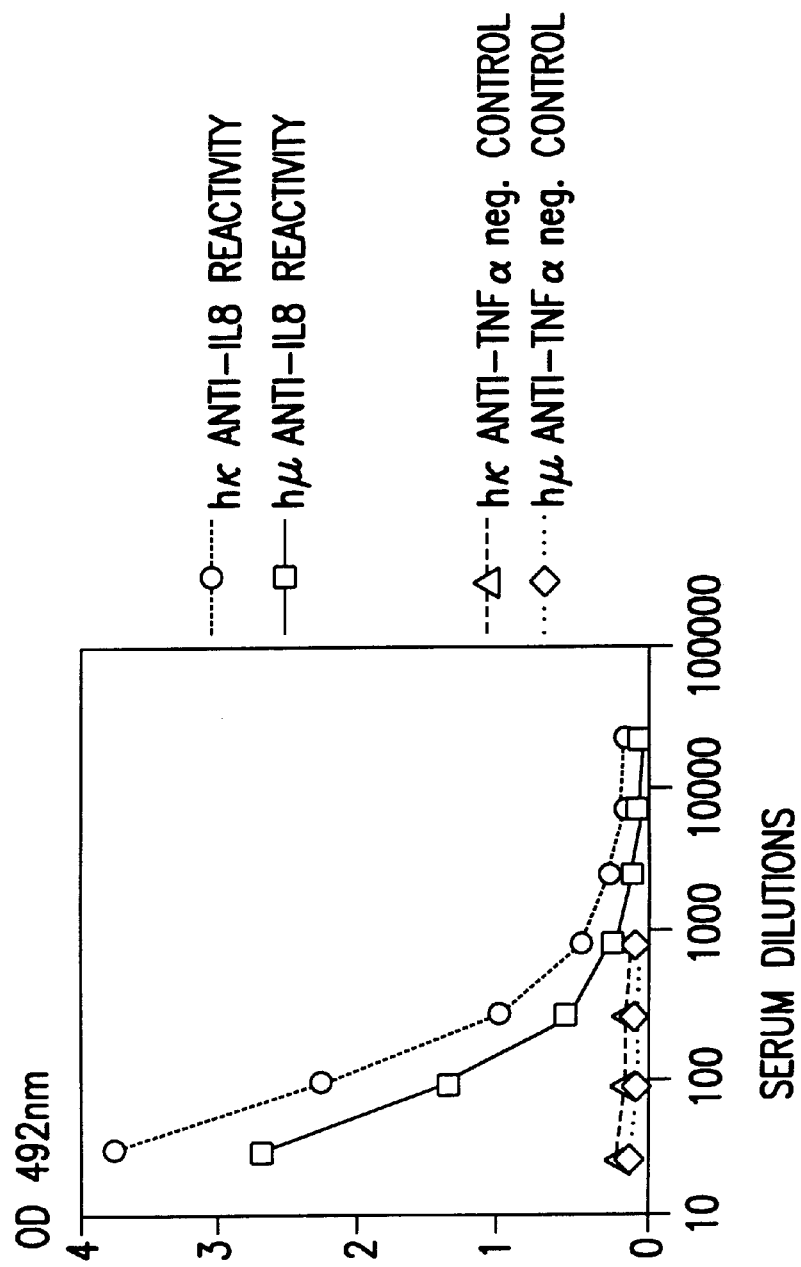
FIG. 14 shows the serum titers of anti-IL-8 antibodies of XenoMouse™ immunized with human IL-8 and which antibodies contain human γ light chains and/or human μ heavy chains.

ELISA assays were performed with respect to the recovered serum, also exactly as described in Example 1, except that the ELISA plates were initially coated using 100 μl/well of recombinant human IL-8 at 0.5mg/ml in the coating buffer. The results obtained for various serum dilutions from XenoMouse™ after 6 injections are shown in FIG. 14. Human anti-IL-8 binding was again shown at serum dilutions having concentrations higher than that represented by a 1:1,000 dilution.

EXAMPLE 9

Preparation of High Affinity Human Monoclonal Antibodies Against Human IL-8

Groups of 4 to 6 XenoMouse™ aged between 8 to 10 weeks old were used for immunization and for hybridoma generation. XenoMouse™ were immunized intraperitoneally with 25 μg of human recombinant-IL-8 (Biosource International, Calif., USA) emulsified in complete Freund's adjuvant (CFA, Sigma) for the primary immunization. All subsequent injections were done with the antigen incorporated into incomplete Freund's adjuvant (IFA, Sigma). For animals used as spleen donors for hybridoma generation a final dose of antigen in phosphate buffer saline (PBS) was given 4 days before the fusion. Serum titers of immunized XenoMouse™ were first analyzed after a secondary dose of antigens, and from there after, following every antigen dose. Test bleeds were performed 6 to 7 days after the injections, by bleeding from the retro-bulbar plexus. Blood was allowed to clot at room temperature for about 2 hours and then incubated at 4° C. for at least 2 hours before separating and collecting the sera.

Generation of hybridomas

Spleen cells obtained from XenoMouse™ previously immunized with antigen, were fused with the non secretory NSO myeloma cells transfected with bcl-2 (NSO-bcl2) as described in Galfre G, et al., *Methods in Enzymology* 73, 3–46, (1981). Briefly, the fusion was performed by mixing washed spleen cells and myeloma cells at a ratio of 5:1 and gently pelleting them by centrifugation at 800Xg. After complete removal of the supernatant the cells were treated with 1 ml of 50% PEG/DMSO (polyethylene glycol MW 1500, 10% DMSO, Sigma) which was added over 1 min., the mixture was further incubated for one minute, and gradually diluted with 2 ml of DMEM over 2 minutes and diluted further with 8 ml of DMEM over 3 minutes. The process was performed at 37° C. with continued gentle stirring. After fusion the cells were resuspended in DMEM, 15% FCS, containing HAT, and supplemented with L glutamine, pen/strep, for culture at 37° C. and 10% CO2 in air. Cells were plated in flat bottomed 96 well microtiter trays. Cultures were maintained in HAT supplemented media for 2 weeks before transfer to HT supplemented media. Cultures were regularly examined for hybrid cell growth, and supernatants from those wells containing hybridomas were collected for a primary screen analysis for the presence of human μ, human gamma 2, and human kappa chains in an antigen specific ELISA as described above. Positive cultures were transferred to 48 well plates and when reaching confluence transferred to 24 well plates. Supernatants were tested in an antigen specific ELISA for the presence of human μ, human gamma 2, and human kappa chains.

As shown in Table 3 several hybridomas secreting fully human monoclonal antibodies with specificity for human IL-8 have been generated from representative fusions. In all of these human monoclonal antibodies the human gamma-2 heavy chain is associated with the human kappa light chain.

TABLE 3

ELISA determination of heavy and light chain composition of anti-IL-8 human monoclonal antibodies generated in XenoMouse ™

| | | | reactivity to hIL8 | | | |
|---|---|---|---|---|---|---|
| Sample ID | lg class | titers | $H_\kappa$ OD (1:1) | m$\lambda$ OD (1:1) | h$\gamma$ OD (1:1) | Total hIgG (ng/ml) |
| Bkgd | | | 0.08 | 0.04 | 0.12 | |
| I8D1.1 | hIgG2 | 500 | 4.12 | 0.04 | 4.09 | 1,159 |
| I8K2.1 | hIgG2 | 200 | 4.18 | 0.18 | 4.11 | 2,000 |
| I8K2.2 | hIgG2 | 1,000 | 4.00 | 0.04 | 4.00 | 4,583 |
| I8K4.2 | hIgG2 | 200 | 3.98 | 0.04 | 3.49 | 450 |
| I8K4.3 | hIgG2 | 200 | 3.80 | 0.05 | 4.09 | 1,715 |
| I8K4.5 | hIgG2 | 1,000 | 4.00 | 0.06 | 4.00 | 1,468 |

Evaluation of kinetic constants of XenoMouse™ hybridomas

In order to determine the kinetic parameters of these antibodies, specifically their on and off rates and their dissociation constants (KD), they were analyzed on the BIAcore instrument (Pharmacia). The BIAcore instrument uses plasmon resonance to measure the binding of an antibody to an antigen-coated gold chip.

BIAcore reagents and instrumentation:

The BIAcore instrument, CM5 sensor chips, surfactant P20, and the amine coupling kit containing N-hydroxysuccinimide (NHS), N-ethyl-N$^1$-(3-diethylaminopropyl)carbodimide (EDC), and ethanolamine were purchased from Pharmaicia Biosensor. Immobilization of human recombinant IL-8 onto the sensor surface was carried out at low levels of antigen density immobilized on the surface and was performed according to the general procedures outlined by the manufacturers. Briefly, after washing and equilibrating the instrument with REPES buffer (HBS; 10 mM HEPES, 150 mM NaCl, 0.05% surfactant P20, pH 7.4) the surface was activated and IL-8 immobilized for the subsequent binding and kinetic studies. The sensor surface was activated with 5 $\mu$l of a mixture of equal volumes of NHS (0.1 M) and EDC (0.1 M) injected at 10 $\mu$l/min across the surface for activation, then 5 $\mu$l of the ligand (human recombinant IL-8) at 12 $\mu$g/ml in 5 mM maleate buffer, pH 6.0 was injected across the activated surface, and finally non-conjugated active sites were blocked with an injection of 35 $\mu$l of 1 M ethanolamine. The surface was washed to remove non-covalently bound ligand by injection of 5 $\mu$l 0.1 M HCl. All the immobilization procedure was carried out with a continuous flow of HBS of 10 $\mu$l/min. About 100 resonance units (RU) of ligand (82 and 139 RU, in separate experiments) were immobilized on the sensor chip, (according to the manufacturers 1,000 RU corresponds to about 1 ng/mm$^2$ of immobilized protein).

These ligand coated surfaces were used to analyze hybridoma supernatants for their specific binding to ligand and for kinetic studies. The best regenerating condition for the analyte dissociation from the ligand in these sensor chips was an injection of 10 $\mu$l 100 mM HCl with no significant losses of binding observed after many cycles of binding and regeneration.

Determination of the dissociation, and association rates and the apparent affinity constants of fully human monoclonal antibodies specific for IL-8

The determination of kinetic measurements using the BIAcore in which one of the reactants is immobilized on the sensor surface was done following procedures suggested by the manufacturers and described in Karlsson et al. "Kinetic analysis of monoclonal antibody-antigen interaction with a new biosensor based analytical system." J. Immunol. Methods (19910 145, 229. Briefly the single site interaction between two molecules A and B is described by the following equation.

$$d[AB]/dt=ka[A][B]-kd[AB]$$

In which B is immobilized on the surface and A is injected at a constant concentration C. The response is a measure of the concentration of the complex [AB] and all concentration terms can be expressed as Response Units (RU) of the BIAcore:

$$dR/dt=kaC(Rmax-R)-kdR$$

where dR/dt is the rate of change of the signal, C is the concentration of the analyte, Rmax is the maximum analyte binding capacity in RU and R is the signal in RU at time t. In this analysis the values of ka and kd are independent of the concentration of immobilized ligand on the surface of the sensor. The dissociation rates (kd) and association rates (ka) were determined using the software provided by the manufacturers, BIA evaluation 2.1. The dissociation rate constant was measured during the dissociation phase that extended for 10 minutes at a constant buffer flow rate of 45 ul/min, after the completion of the injection of the hybridoma supernatants onto the surface containing immobilized IL-8. The association phase extended over 1.25 minutes at a flow rate of 45 ul/min and the data was fitted into the model using the previously determined kd values. At least two surfaces with different levels of immobilized ligand were used in which different concentrations of anti IL-8 hybridoma supernatants were tested for binding and analyzed for kinetic data. The kinetic constants determined on these two surfaces are presented in Table 4. The affinities were determined to vary, ranging from $7\times10^{-11}$ to $2\times10^{-9}$ M. This compares very favorably with the affinities of murine monoclonal antibodies derived from normal mice.

TABLE 4

Kinetic constants of fully human monoclonal antibodies (IgG2, kappa) derived from XenoMouse ™ II-a with specificity to human IL-8, determined by BIAcore.

| Hybridoma | association rate ka (M$^{-1}$ s$^{-1}$) | dissociation rate kd ($_s^{-1}$) | Dissociation Constant KD (M) = kd/ka | BIAcore surface h-IL-8 [RU] |
|---|---|---|---|---|
| I8D1-1 | 3.36 x 106 | 2.58 x 10−4 | 7.70 x 10−11 | 81 |
| | 2.80 x 106 | 1.73 x 10−4 | 6.20 x 10−11 | 134 |
| I8K2-1 | 4.38 x 105 | 6.73 x 10−4 | 1.54 x 10−9 | 81 |
| | 3.83 x 105 | 6.85 x 10−4 | 1.79 x 10−9 | 134 |
| I8K2-2 | 5.24 x 105 | 2.26 x 10−4 | 4.30 x 10−10 | 81 |
| | 4.35 x 105 | 2.30 x 10−4 | 5.30 x 10−10 | 134 |
| I8K4-2 | 5.76 x 106 | 8.17 x 10−4 | 1.42 x 10−10 | 81 |
| | 1.95 x 106 | 3.84 x 10−4 | 1.96 x 10−10 | 134 |
| I8K4-3 | 2.66 x 106 | 7.53 x 10−4 | 2.83 x 10−10 | 81 |
| | 1.46 x 106 | 5.72 x 10−4 | 3.90 x 10−10 | 134 |
| I8K4-5 | 4.00 x 105 | 9.04 x 10−4 | 2.26 x 10−9 | 81 |
| | 1.70 x 105 | 4.55 x 10−4 | 2.68 x 10−9 | 134 |

Methods for isolation of human neutrophils and assays for antibody activity

The primary in vivo function of IL-8 is to attract and activate neutrophils. Neutrophils express on their surface two distinct receptors for IL-8, designated the A receptor and the B receptor. In order to determine whether the fully human antibodies could neutralize the activity of IL-8, two different in vitro assays were performed with human neutrophils. In one assay, the ability of the antibodies to block binding or radiolabelled IL-8 to neutrophil IL-8 receptors was tested. In a second assay, the antibodies were tested for their ability to block an IL-8-induced neutrophil response, namely the upregulation of the integrin Mac-1 on the neutrophil surface. Mac-1 is composed of two polypeptide chains, CD11b and CD18. Typically, anti-CD11b antibodies are used for its detection.

Isolation of neutrophils

Figure 15A:
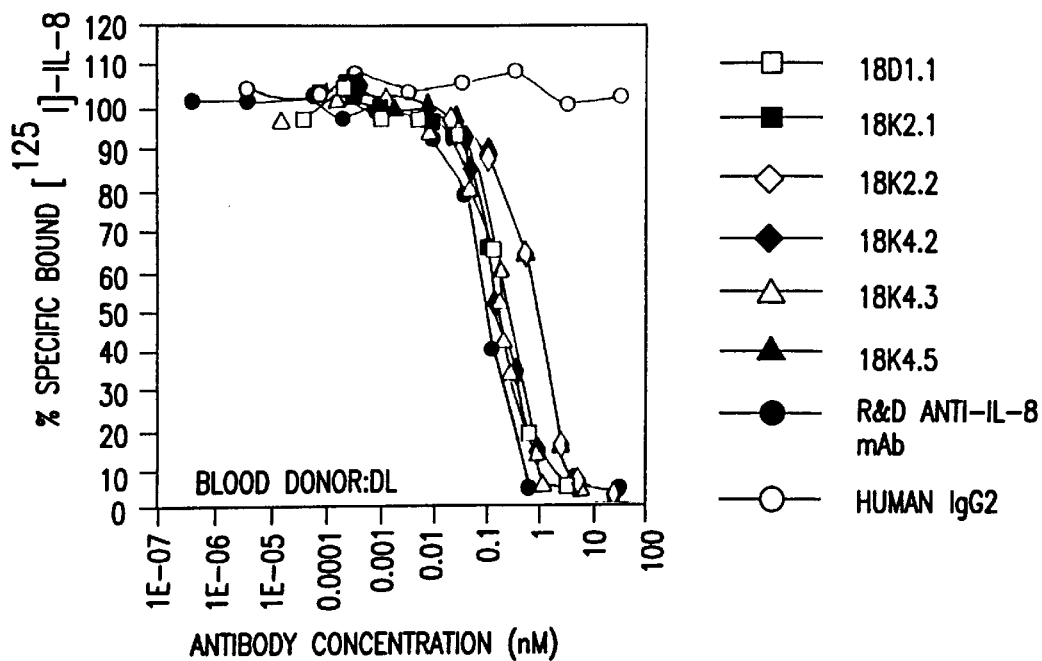
FIG. 15(A&B) Inhibition of IL-8 binding to human neutrophils by monoclonal anti-human-IL-8 antibodies.
Figure 15B:
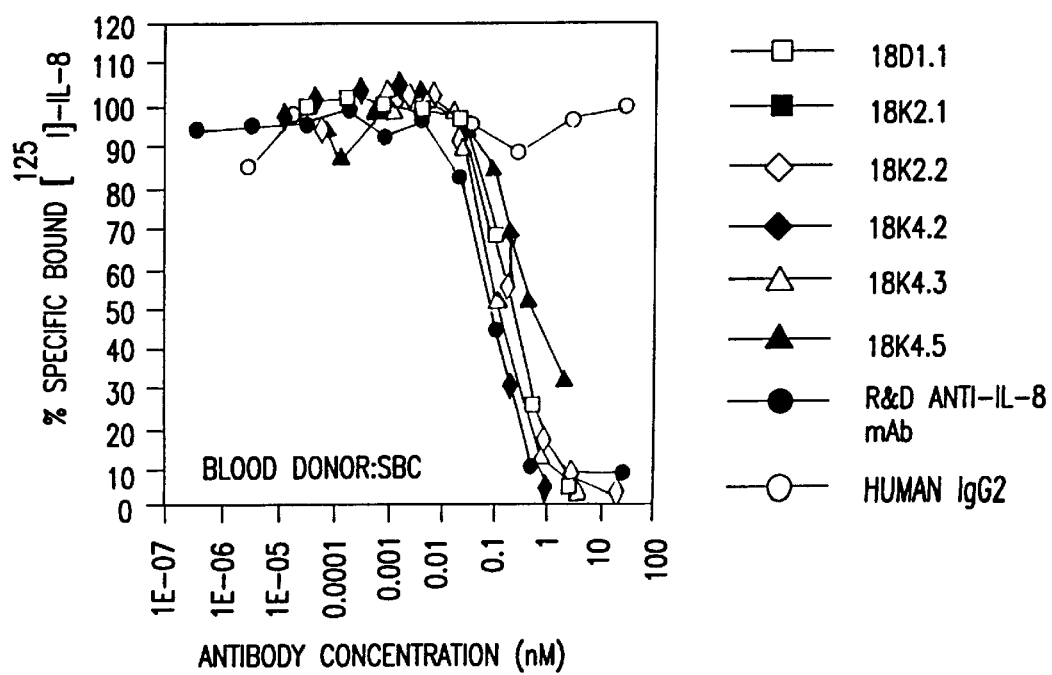

Human neutrophils are isolated from either freshly drawn blood or buffy coat. Human blood is collected by venipuncture into sterile tubes containing EDTA. Buffy coats are obtained from Stanford Blood Bank. They are prepared by centrifuging anticoagulated blood (up to 400 ml) in plastic bags at 2600 xg for 10 min at 20° C. with the brake off. The plasma supernatant is aspirated out of the bag and the buffy coat, i.e., the upper cell layer (40–50 ml/bag) is collected. One unit of buffy coat (40–50 ml) is diluted to final volume of 120 ml with $Ca^{2+}$, $Mg^{2+}$-free PBS. 30 milliliters of blood or diluted buffy coat are transferred into 50-ml centrifuge tubes on top of a 20-ml layer of Ficoll-Paque Plus (Pharmacia Biotech). The tubes are centrifuged at 500 xg for 20 min at 20° C. with brake off. The supernatant, the mononuclear cells at the interface, and the layer above the pellet are carefully withdrawn. To completely remove the mononuclear cells, the cell pellet containing neutrophils and erythrocytes is resuspended with 5 ml of PBS and transferred into clean 50-ml tubes. The cells are washed in $Ca^{2+}$, $Mg^{2+}$-free PBS (300 xg for 5 min at 4° C.). The erythrocytes are then lysed with ammonium chloride. The cells are resuspended in 40 ml of an ice-cold solution containing 155 mM $NH_4Cl$ and 30 10 nM EDTA, pH 7.2–7.4. The tubes are kept on ice for 10 min with occasional mixing and then centrifuged at 300 xg for 5 min at 4° C. The pellet is resuspended in PBS and washed once (300 xg for 5 min at 4° C). If erythrocyte lysis appears incomplete, the treatment with ammonium chloride is repeated. The neutrophils are again washed and finally suspended either in assay medium (RPMI-1640 supplemented with 10t fetal calf serum, 2 mM L-glutamine, $5 \times 10^{-5}$ 2-mercapthoethanol, 1X non-essential amino acids, 1 mM sodium pyruvate and 10 mM Hepes) at a density of $3 \times 10^7$ cells/ml or in a binding buffer (PBS containing 0.1% bovine serum albumin and 0.02% $NaN_3$), at a density of $6 \times 10^6$ cells/ml IL-8 receptor binding assay Multiscreen filter plates (96-well, Millipore, MADV N6550) were pretreated with a PBS binding buffer containing 0.1% bovine serum albumin and 0.02% $NaN_3$ at 25° C. for 2 hours. A final volume of 150 µl, containing $4 \times 10^5$ neutrophils, 0.23 nM $[^{125}I]$-human-IL-8 (Amersham, IM-249) and varying concentrations of antibodies made up in PBS binding buffer, was added to each well, and plates were incubated for 90 min at 4° C. Cells were washed 5 times with 200 µl of ice-cold PBS, which was removed by aspiration. The filters were air-dried, 3.5 ml of scintillation fluid was added (Beckman Ready Safe) and filters were counted on a Beckman LS6000IC counter. The data obtained is presented as % specific bound $[I^{125}]$-IL-8, which is calculated as the cpm in the presence of antibody divided by the cpm in the presence of PBS binding buffer only and multiplied by 100 (FIG. 15). All six of the human anti-IL-8 monoclonals tested blocked IL-8 binding to human neutrophils.

Neutrophil CD11b (Mac-1) expression assay

Human IL-8 at a final concentration of 10 nM was preincubated with varying concentrations of monoclonal antibodies at 4° C. for 30 minutes and at 37° C. for an additional 30 min. Neutrophils ($4 \times 10^5$/well) were exposed to IL-8 in the presence or absence of antibodies at 4° C. for 90 min, and incubated with PE-conjugated mouse-anti-human-CD11b (Becton Dickinson) for 45 min at 4° C. The cells were washed with ice-cold PBS containing 2% fetal calf serum. Fluorescence was measured on a Becton Dickinson FACscan cell analyzer. A mouse monoclonal antibody against human CD11b obtained from R&D System, Inc. was used as a positive control while the purified myeloma human IgG2 (Calbiochem) was used as a negative control in the experiments. The expression levels of CD11b on neutrophils were measured and expressed as the mean fluorescence channel. The mean fluorescence channel derived form the negative control antibody was subtracted from those of experimental samples.

$$\% \text{ inhibition} = \frac{\text{mean fluorescence in presence of IL-8 only} - \text{mean fluorescence in the presence of antibodies}}{\text{mean fluorescence in the presence of IL-8 only} - \text{mean fluorescence in the presence of human IgG2}} \times 100$$

As shown in Table 5, five of the six antibodies blocked upregulation of CD11b to some degree, with three of the five giving complete blocking.

TABLE 5

Inhibition of CD11b expression on human neutrophils by monoclonal antibodies against IL-8.

| Antibody | Concentration (nM) | Inhibition of CD11b expression (%) |
| --- | --- | --- |
| R&D anti-IL8 | 333 | 100 |
| I8K1.1 | 6 | 100 |
| I8K2.1 | 10 | 60 |
| I8K2.2 | 32 | 100 |
| I8K4.2 | 3 | 10 |
| I8K4.3 | 8 | 100 |
| I8K4.5 | 5 | 0 |
| Human IgG2 | 33 | 0 |

Background of CD11b expression is 670 (mean fluorescence) while CD11b expression in the presence of 10 nM of human IL-8 is 771.

Sequence analysis of Immunoglobulin transcripts derived from anti-hIL-8 hybridomas.

All sequences were derived by direct sequencing of PCR fragments generated from RT-PCR reactions of RNA prepared from hybridomas D1.1, K2.2, K4.2 and K4.3, using human $V_H$ and human $V_\kappa$ family specific primers (Marks et. al. 1991; Euro J. Immunol 21;985–991) and a primer specific for either the human gamma 2 constant region (MG-40d; 5'GCTGAGGGAGTAGAGTCCTGAGGACTGT-3') (SEQ ID NO:21) or human kappa constant region (HKP2; Green et al 1994; Nature Genetics 7: 13–21)). In FIG. 16 A–H, both strands of the four clones were sequenced and analyzed to generate the complete sequence. All sequences were analyzed by alignments to the "V BASE sequence directory", Tomlinson et al., MRC Centre for Protein Engineering, Cambridge, UK. The variable and joining regions are indicated by brackets []. Nucleotides containing an "N" indicate uncertainty in the generated sequence.

Based on sequence alignments with sequences found in the V-base database the heavy chain transcript from hybridoma D1.1 has a human $V_H4$-21(DP-63) variable region (7 point mutations were observed compared to the germline sequence), a human 21-10rc D segment, a human $J_H3$ joining region and a human gamma 2 constant region. See FIG. 16A.

The kappa light chain transcript from hybridoma D1.1 is comprised of a human kappa variable region with homology to $V_\kappa$ 08/018 (DPK1) (16 point mutations were observed when compared to the germline sequence) a human JX3 joining region, and a human kappa constant region. See FIG. 16B.

Based on sequence alignments with sequences found in the V-base database the heavy chain transcript from hybridoma K2.2 has a human $V_H3$-30 variable region (3 point mutations were observed compared to the germline sequence), a human IR3rc D segment, a human $J_H4$ joining region and a human gamma 2 constant region. See FIG. 16C.

The kappa light chain transcript from hybridoma K2.2 is comprised of a human kappa variable region with homology to $V_\kappa$IV (B3; DPK24) (9 point mutations were observed when compared to the germline sequence), a human $J_K3$ joining region, and a human kappa constant region. See FIG. 16D.

Based on sequence alignments with sequences found in the V-base database the heavy chain transcript from hybridoma K4.2 has a human $V_H4$-34 variable region (8 point mutations were observed compared to the germline sequence), a human K1 D segment, a human $J_H4$ joining region and a human gamma 2 constant region. See FIG. 16E.

The kappa light chain transcript from hybridoma K4.2 is comprised of a human kappa variable region with homology to $V_\kappa$ 08/018 (DPK1) (6 point mutations were observed when compared to the germline sequence), a human $J_\kappa4$ joining region, and a human kappa constant region. See FIG. 16F.

Based on sequence alignments with sequences found in the V-base database the heavy chain transcript from hybridoma K4.3 has a human $V_H5$-51 (DP-73) variable region, a human M5-a/M5-b D segment, a human $J_H4$ joining region and a human gamma 2 constant region. See FIG. 16G.

The kappa light chain transcript from hybridoma K4.3 is comprised of a human kappa variable region with homology to $V_\kappa$ 02/012 (DPK9) (9 point mutations were observed when compared to the germline sequence), a human $J_\kappa4$ joining region, and a human kappa constant region. See FIG. 16H.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Biological Deposits yH1C contained in S. cerivisiae was deposited with the American Type Culture Collection ("ATCC"), 12301 Parklawn Drive, Rockville Md. 20852, USA, on Apr. 26, 1996, and given ATCC accession no. 74367. The deposit of this YAC is for exemplary purposes only, and should not be taken as an admission by the Applicant that such deposit is necessary for enablement of the claimed subject matter.

The current address of the ATCC is shown below: American Type Culture Collection 10801 University Boulevard Manassas, Va. 20110 Phone 703-365-2700 Facsimile 703-365-2750

What is claimed is:

1. A transgenic mouse wherein all of the somatic and germ cells comprise a DNA fragment of human chromosome 14 from the five most proximal $V_H$ gene segments, continuing through the D segment genes, the J segment genes and the constant region genes through Cδ of the human immunoglobulin heavy chain locus, wherein said fragment does not contain a Cγ gene, and wherein said fragment is operably linked to a human Cγ2 region gene;

said transgenic mouse producing fully human IgG2 heavy chains specific for a desired antigen when immunized with said desired antigen.

2. The transgenic mouse according to claim 1, wherein all of the somatic and germ cells of said transgenic mouse further comprise a fragment of human chromosome 2 comprising $V_\kappa$, $J_\kappa$ and $C_\kappa$ gene segments of an immunoglobulin kappa light chain locus, said transgenic mouse producing fully human IgG2 antibodies specific for a desired antigen when immunized with said desired antigen.

3. The transgenic mouse according to claim 1, wherein all of the somatic and germ cells comprise the human DNA contained in the yH1C YAC having ATCC accession no. 74367.

4. The transgenic mouse according to claim 2, wherein all of the somatic and germ cells comprise the human DNA contained in the yH1C YAC having ATCC accession no. 74367.

5. The transgenic mouse according to claim 3, wherein said fragment of human chromosome 2 extends from the three most proximal $V_\kappa$ gene segments, continuing through the $J_\kappa$ and $C_\kappa$ gene segments, through the human kappa deleting element.

6. The transgenic mouse according to claim 4, wherein said fragment of human chromosome 2 extends from the three most proximal $V_\kappa$ gene segments, continuing through the $J_\kappa$ and $C_\kappa$ gene segments, through the human kappa deleting element.

7. The transgenic mouse and progeny according to any one of claims 1–6, wherein all of the somatic and germ cells further comprise:

a) inactivated endogenous immunoglobulin heavy chain loci in which all of the J segment genes are deleted to prevent rearrangement and to prevent formation of a transcript of a rearranged locus and the expression of an endogenous immunoglobulin heavy chain; and b) inactivated endogenous immunoglobulin light chain loci in which the $C_\kappa$ gene is deleted to prevent expression of an endogenous immunoglobulin light chain;

wherein said transgenic mouse and progeny lack expression of endogenous immunoglobulin heavy chains.

8. A method for producing a fully human IgG antibody specific for a desired antigen, comprising:

(a) immunizing a transgenic mouse according to any one of claims 1–7 with said desired antigen; and (b) recovering the antibody.

9. The method according to claim 8, wherein the desired antigen is selected from the group consisting of: leukocyte markers; histocompatibility antigens; integrins; adhesion molecules; interleukins; interleukin receptors; chemokines; growth factors; growth factor receptors; interferon receptors; immunoglobulins and their receptors; tumor antigens; allergens; viral proteins; toxins; blood factors; enzymes; ganglioside GD3, ganglioside GM2; LMP1, LMP2; eosinophil major basic protein, eosinophil cationic protein; pANCA; Amadori protein; Type IV collagen; glycated lipids; γ-interferon; A7; P-glycoprotein; Fas (AFO-1) and oxidized-LDL.

10. The method according to claim 8, wherein the desired antigen is human IL-8.

11. The method according to claim 8, wherein the desired antigen is PTHrp.

12. The yHlC YAC having ATCC accession number 74367.

* * * * *